United States Patent [19]

Domagala et al.

[11] Patent Number: 5,929,114
[45] Date of Patent: Jul. 27, 1999

[54] ARYLTHIO COMPOUNDS

[75] Inventors: John Michael Domagala, Canton; Edward Faith Elslager, Ann Arbor; Rocco Dean Gogliotti, Pinckney, all of Mich.

[73] Assignee: Warner-Lambert Company, Morris Plains, N.J.

[21] Appl. No.: 08/857,116

[22] Filed: May 15, 1997

Related U.S. Application Data

[62] Division of application No. 08/474,875, Jun. 7, 1995, Pat. No. 5,668,291, which is a division of application No. 08/446,917, Jun. 1, 1995, Pat. No. 5,734,081, which is a continuation-in-part of application No. 08/286,816, Aug. 5, 1994, Pat. No. 5,463,122.

[51] Int. Cl.$^6$ .................................................. A01N 37/20
[52] U.S. Cl. .......................... 514/562; 514/210; 514/211; 514/213; 514/214; 514/215; 514/221; 514/222.8; 514/223.8; 514/224.2; 514/226.8; 514/227.5; 514/228.8; 514/229.2; 514/230.5; 514/231.2; 514/232.2; 514/233.2; 514/233.5; 514/235.5; 514/241; 514/246; 514/248; 514/249; 514/252; 514/255; 514/256; 514/258; 514/259; 514/300; 514/301; 514/302; 514/303; 514/316; 514/383; 514/385; 514/403; 514/408; 514/422; 514/423; 514/424; 514/426; 514/427; 514/428; 514/431; 514/432; 514/433; 514/438; 514/439; 514/443; 514/444; 514/445; 514/450; 514/451; 514/456; 514/461; 514/464; 514/513; 514/533; 514/564; 514/616; 514/617; 514/618; 514/619; 514/620

[58] Field of Search ..................... 514/616, 617, 514/564, 566, 618, 601, 619, 620, 316, 422, 210, 211, 213, 214, 215, 221, 222.8, 223.8, 224.2, 226.8, 227.5, 228.8, 229.2, 230.5, 231.2, 232.2, 233.2, 233.5, 235.5, 241, 246, 248, 249, 252, 255, 256, 258, 259, 300, 301, 302, 303, 383, 385, 403, 408, 423, 424, 426, 427, 428, 431, 432, 433, 438, 439, 443; 514/444, 445, 450, 451, 456, 461, 464

[56] References Cited

U.S. PATENT DOCUMENTS

| | | | |
|---|---|---|---|
| 3,012,039 | 12/1961 | Morley et al. | 260/304 |
| 3,517,022 | 6/1970 | Miller et al. | 260/304 |
| 3,574,858 | 4/1971 | Volpp | 424/324 |
| 3,661,974 | 5/1972 | Grivas | 260/470 |
| 3,663,616 | 5/1972 | Grivas | 260/558 S |
| 3,736,280 | 5/1973 | Grivas | 260/22 A |
| 3,761,489 | 9/1973 | Grivas | 260/304 |
| 3,786,150 | 1/1974 | Lee et al. | 424/270 |
| 3,965,107 | 6/1976 | Rainey et al. | 260/294.8 |
| 4,156,729 | 5/1979 | Böshagen et al. | 424/270 |
| 4,295,887 | 10/1981 | Buckley et al. | 106/18.33 |
| 4,479,950 | 10/1984 | Menard et al. | 424/248.5 |
| 4,705,805 | 11/1987 | Yamada et al. | 514/548 |
| 4,727,188 | 2/1988 | Jaedicke | 564/154 |
| 4,975,367 | 12/1990 | Albarella et al. | 435/11 |

FOREIGN PATENT DOCUMENTS

| | | |
|---|---|---|
| 0062827 | 10/1982 | European Pat. Off. . |
| 861326 | 5/1978 | France . |
| 477476 | 3/1992 | Japan . |
| 1306493 | 2/1973 | United Kingdom . |
| 1560726 | 2/1980 | United Kingdom . |
| 92/06683 | 4/1992 | WIPO . |
| 9206683 | 4/1992 | WIPO . |
| 9306832 | 4/1993 | WIPO . |

OTHER PUBLICATIONS

Yamada et al., Chem. Pharm. Bull., vol. 33, No. 3, 1985, pp. 1214–1220.
Nandi and Dash, Agr. Biol. Chem., vol. 40, No. 11, 1976, pp. 2143–2149.
El–Barbary et al., Tetrahedron, vol. 36, No. 22, 1980, pp. 3309–3315.
Die Pharmazie, vol. 22, No. 11, 1967, Wagner et al., pp. 605–620.
Chemische Berichte, vol. 99, No. 8, 1966, Böshagen, pp. 2566–2571.
Il Farmaco, Edizione Scientifica, vol. 29, No. 1, 1974, Vitali et al., pp. 27–36.
Il Farmaco, Edizione Scientifica, vol. 32, No. 7, 1977, Montanari et al., pp. 539–548.
Il Farmaco, vol. 47, No. 2, 1992, Zani, pp. 219–228.
Il Farmaco, vol. 44, No. 4, 1989, Nacci et al., pp. 423–433.
Bulletin de la Société Chimique de France, No. 3, 1962, Moreau and Delacoux, pp. 502–505.
Chimie Thérapeutique, vol. 8, No. 3, 1973, Delacoux et al., pp. 303–307.
Journal of Heterocyclic Chemistry, vol. 7, No. 5, 1970, Heindel and Ko, pp. 1007–1011.

(List continued on next page.)

*Primary Examiner*—Dwayne C. Jones
*Attorney, Agent, or Firm*—Charles W. Ashbrook

[57] ABSTRACT

Arylthiol and dithiobisarylamide antibacterial and antiviral agents have the general formula

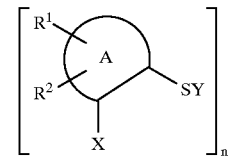

where A is monocyclic or bicyclic aryl which can contain up to 3 heteroatoms selected from O, S, and N, $R^1$ and $R^2$ are substituent groups, X is

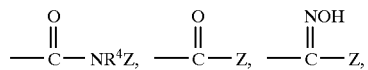

or $SO_2NR^4Z$, Y is H or SZ when n is 1, a single bond when n is 2; $R^4$ and Z can be hydrogen or alkyl.

6 Claims, No Drawings

OTHER PUBLICATIONS

*Journal of Medicinal Chemistry*, vol. 28, No. 3, 1985, Menard et al., pp. 328–332.

*Journal of Heterocyclic Chemistry*, vol. 25, No. 3, 1988, Nacci et al., pp. 1007–1013.

*J. Org. Chem.*, vol. 43, No. 6, 1978, Abramovitch et al., pp. 1218–1226.

*Journal of the Society of Dyers and Colourists*, vol. 57, 1941, Hopper et al., pp. 6–9.

*Il Farmaco, Edizione Scientifica*, vol. 14, No. 9, 1959, Gialdo et al., pp. 648–665.

*Il Farmaco, Edizione Scientifica*, vol. 14, No. 11, 1959, Gialdo et al., pp. 751–770.

*Il Farmaco, Edizione Scientifica*, vol. 15, No. 12, 1960, Gialdi et al., pp. 835–841.

*Il Farmaco, Edizione Scientifica*, vol. 16, No. 6, 1961, Gialdi et al., pp. 411–437.

*Il Farmaco, Edizione Scientifica*, vol. 18, No. 10, 1963, Ponci et al., pp. 732–749.

*Il Farmaco, Edizione Scientifica*, vol. 19, No. 3, 1964, Ponci and Baruffini, pp. 246–253.

*Il Farmaco, Edizione Scientifica*, vol. 19, No. 3, 1964, Ponci et al., pp. 254–268.

*Il Farmaco, Edizione Scientifica*, vol. 22, No. 11, 1967, Ponci et al., pp. 935–946.

*Il Farmaco, Edizione Scientifica*, vol. 22, No. 12, 1967, Ponci et al., pp. 989–998.

*Il Farmaco, Edizione Scientifica*, vol. 22, No. 12, 1967, Ponci et al., pp. 999–1010.

*Il Farmaco, Edizione Scientifica*, vol. 23, No. 5, 1968, Vitali et al., pp. 468–476.

*Gazzetta Chimica Italiana*, vol. 90, 1960, Passerini and Purrello, pp. 1277–1289.

*Phytochemistry*, vol. 29, No. 9, 1990, Ricci et al., pp. 2787–2791.

PB93–100626, Levine et al., pp. 1–23, 1993.

*Article*, vol. 81, No. 8, Apr. 19, 1989, Weislow et al., pp. 577–586.

Okachi, et al., *J. Med. Chem.*, vol. 28, No. 12, pp. 1772–1779 (1985).

Carmelino, et al., *Eur. J. Med. Chem.*, vol. 29, pp. 743–751 (1994).

ARYLTHIO COMPOUNDS

This is a divisional of Ser. No. 08/474,875 filed Jun. 7, 1995, now U.S. Pat. No. 5,668,291 which is a divisional of Ser. No. 08/446,917 filed Jun. 1, 1995 now U.S. Pat. No. 5,734,081, which is a continuation-in-part of Ser. No. 08/286,816 filed Aug. 5, 1994, now U.S. Pat. No. 5,463,122.

TECHNICAL FIELD OF THE INVENTION

This invention concerns compounds characterized as arylthio derivatives, and more particularly, as arylthiols and aryl disulfides. The compounds are useful as antibacterial and antiviral agents. The compounds are especially useful in inhibiting the growth or replication of retroviruses such as human immunodeficiency virus 1 and 2 (HIV 1 and HIV 2), Simian immunodeficiency virus (SIV), Rous sarcoma virus, and human T-lymphotropic viruses 1 and 2 (HTLV 1 and HTLV 2). The compounds are useful in treating bacterial infections and viral infections.

BACKGROUND OF THE INVENTION

Bacterial infections have long been treated with effective agents such as quinolones, penicillins, and cephalosporins. However, a growing number of bacteria are becoming resistant to conventional agents, and accordingly, new drugs are needed to treat resistant strains.

Unlike bacterial infections, viral diseases have not had a wide range of agents available for treatments. While many viral infections have afflicted mankind for many years, certain diseases have only recently attracted attention due to severity and limited treatments available. Of particular importance is the viral infection known as acquired immune deficiency syndrome (AIDS).

AIDS is a very serious disease worldwide. AIDS infections have increased dramatically within the past several years. Estimates of reported cases in the very near future also continue to rise dramatically. Consequently, there is a great effort to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct types of HIV have been described to date, namely HIV-1 and HIV-2. The acronym HIV will be used herein to refer to HIV viruses generically.

HIV is known to exert a profound cytopathic effect on the CD4+ helper/inducer T-cells, thereby severely compromising the immune system. HIV infection also results in neurological deterioration and, ultimately in the death of the infected individual.

The field of viral chemotherapeutics has developed in response to the need for agents effective against retroviruses, in particular HIV. There are many ways in which an agent can exhibit antiretroviral activity. For example, HIV requires at least five viral proteins for replication: reverse transcriptase (RT), protease (PR), transactivator protein (TAT), integrase (IN), and regulator of virion-protein expression (REV). In addition, there are several structural proteins that play an important role in the replication and cell to cell transfer of HIV. These include the CD4 binding protein GP120, the nucleocapsid protein NCp7, and the fusion protein GP41. Accordingly, viral replication could theoretically be inhibited through binding or inhibiting any one or all of the proteins involved in the viral replication cycle.

A large number of antiretroviral agents, such as AZT, ddC, TIBO, and the like are known to inhibit RT. There also exist antiviral agents that inhibit transactivation by inhibiting the function of the protein TAT.

A useful approach being investigated recently for potential use in the treatment of AIDS is the development of synthetic peptides as inhibitors of the retroviral protease. It is known that retroviruses, including HIV, express their genetic content by directing the synthesis of a polyprotein by the host. The polyprotein is a precursor molecule, which is processed through proteolysis to generate essential viral enzymes and structural proteins. The virally encoded protease is contained within the polyprotein and is responsible for cleaving the polyprotein to yield mature viral proteins. Since the protease is known to be required for viral replication, it has been a therapeutic target for the development of AIDS drugs.

These efforts have generated over 50 potent inhibitors of the protease. Several of these inhibitors are scheduled for clinical trials.

Other major efforts are underway to inhibit viral entry into target cells by identifying chemical entities that block the viral receptor. The viral fusion protein has recently been targeted for this approach. In addition, the nucleocapsid protein NCp7 has been recognized as an essential viral protein and its inhibition has been reported.

An object of this invention is to provide a new series of organic molecules which have been found to exhibit excellent antiviral activity in tests recognized to be predictive of agents useful to combat AIDS. A further object of the invention is to provide compounds having antibacterial activity. The invention additionally provides pharmaceutical compositions which are useful in treating viral and bacterial infections, and also provides a therapeutic method for treating such infections.

SUMMARY OF THE INVENTION

This invention provides arylthio compounds having antibacterial and antiviral activity. More particularly, the invention provides compounds of the Formula I $$\left[ \begin{array}{c} R^1 \\ R^2 \end{array} \!\!\!\! \diagdown\!\!\!\!\!\! \bigcirc\!\!\!\!\!\! \diagup \!\!\!\! \begin{array}{c} A \\ SY \\ X \end{array} \right]_n \quad I$$

wherein:

n is 1 or 2;

X is

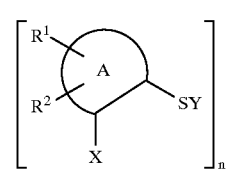

or $SO_2NR^4Z$;

Y is hydrogen or SZ when n is 1, and is a single bond when n is 2;

Z is hydrogen, halo, $C_1$–$C_6$ alkyl, $COC_1$–$C_6$ alkyl, $C_3$–$C_6$ cycloalkyl-$(CR^5R^6)_m$—, phenyl-$(CR^5R^6)_m$—, or Het-$(CR^5R^6)_m$—;

A is a monocyclic ring having 5 or 6 ring atoms, or a bicyclic ring having from 9 to 12 ring atoms, the ring atoms being selected from carbon and optionally up to 3 heteroatoms selected from O, S, and N;

$R^1$ and $R^2$ independently are hydrogen, halo, $C_1$–$C_6$ alkyl, O-$C_1$–$C_6$ alkyl, $C_3$–$C_6$ cycloalkyl, hydroxy, nitro, cyano, phenyl-$(CR^5R^6)_m$—, Het-$(CR^5R^6)_m$—, $NR^3R^4$, $NR^3COR^4$, $CO_2R^3$, $CONR^3R^4$, $S(O)_mR^3$, $S(O)_mNR^3R^4$, $COR^3$, or taken together are oxo (O=) or methylene dioxy (—O—$CH_2$—O—);

m is 0, 1, or 2;

$R^3$ and $R^4$ independently are hydrogen, $C_1$–$C_6$ alkyl, $C_3$–$C_6$ cycloalkyl, phenyl-$(CR^5R^6)_m$—, Het-$(CR^5R^6)_m$—;

$R^5$ and $R^6$ independently are hydrogen, $C_1$–$C_6$ alkyl, hydroxy, COOH, amino, $CONR^3R^4$, or cyano;

wherein the foregoing alkyl, cycloalkyl, phenyl, and Het groups may optionally be substituted with from 1 to 3 groups selected from halo, $C_1$–$C_6$ alkyl, $C_1$–$C_6$ alkoxy, trifluoromethyl, hydroxy, cyano, nitro, $NR^3R^4$, $NR^3COR^4$, $CO_2R^3$,

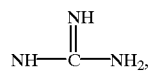

$CONR^3R^4$, $S(O)_mR^3$, $PO_4(R^3)_3$, $S(O)_mNR^3R^4$, and $COR^3$, where m, $R^3$, and $R^4$ are as defined above;

and the pharmaceutically acceptable salts and solvates thereof.

In a preferred embodiment, the arylthio compounds have Formula I wherein A is a monocyclic ring having 6 ring atoms, one or two of which are optionally heteroatoms selected from O, S, and N, ideally N. Especially preferred are compounds of the formulas

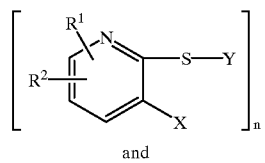

and

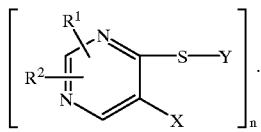

Further preferred compounds are those wherein n is 2 and Y is a bond. Such compounds have the formula

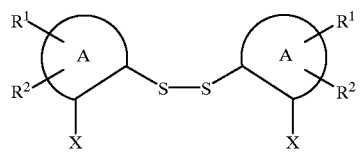

wherein A, $R^1$, $R^2$, and X are as defined above.

Another preferred group of compounds are those of Formula I wherein X is

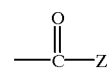

where Z is halo such as chloro. Such compounds have the formula

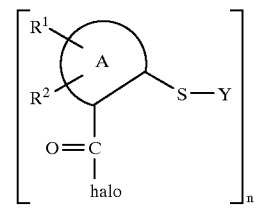

and are particularly useful as intermediates in the synthesis of other invention compounds.

The most preferred antiretroviral agents of the invention have the formula

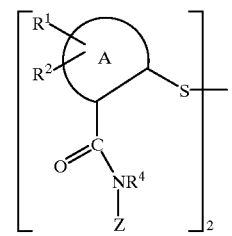

where $R^1$, $R^2$, A, $R^4$, and Z are as defined above. Within this group, the most preferred compounds are those where A is phenyl, pyridyl, or pyrimidinyl, e.g.,

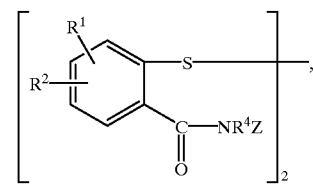

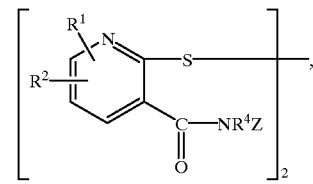

and

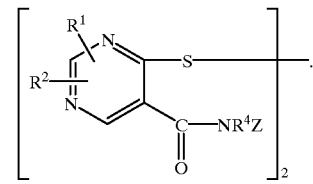

An especially preferred group of compounds have Formula I wherein X is

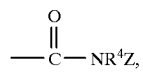

where R⁴ is hydrogen and Z is carboxy substituted alkyl or phenyl-(CR⁵R⁶)ₘ—, and where phenyl is substituted with S(O)ₘNR³R⁴. Especially preferred are Z groups having the formulas

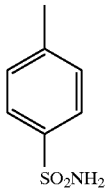

and $C_1$–$C_6$ alkyl substituted with 1 or 2 carboxy groups, e.g.,

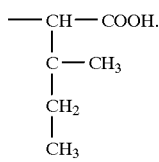

Another especially preferred group of compounds have Formula Ia

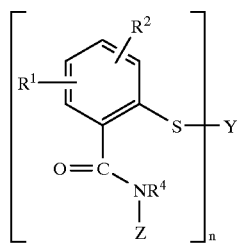

wherein:
n is 1 or 2;
Y is hydrogen when n is 1, and is a single bond when n is 2;
R¹ and R² independently are hydrogen, halo, $C_1$–$C_6$ alkyl, hydroxy, $C_1$–$C_6$ alkoxy, carboxy, $C_1$–$C_6$ alkoxycarbonyl, nitro, or NR³R⁴, where R³ and R⁴ independently are hydrogen or $C_1$–$C_6$ alkyl;
Z is hydrogen, $C_1$–$C_6$ alkyl, $C_3$–$C_6$ cycloalkyl, where said alkyl and cycloalkyl groups may have 1 or 2 substituents selected from hydroxy, halo, nitro, NR³R⁴, and carboxy; or where Z is

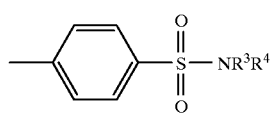

where R³ and R⁴ are as defined above;
and pharmaceutically acceptable salts and solvates thereof.

A preferred group of compounds are thioaryl carboxamides defined by the Formula II

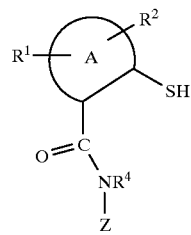

where R¹, R²₁ R⁴₁ A and Z are as defined above. Especially preferred are compounds of the formula

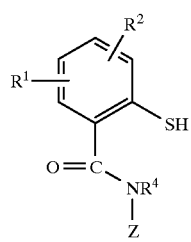

Another preferred group of compounds are dithiobisaryl carboxamides having the Formula III

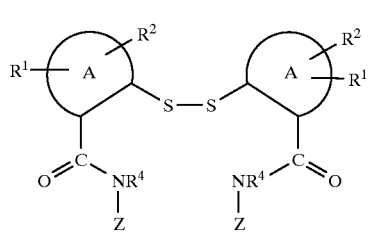

where R¹, R², R⁴, A and Z are as defined above. Especially preferred are compound of the formula

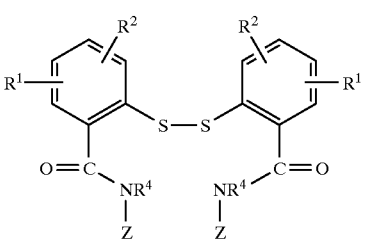

The most preferred compounds are those of the above formulas wherein Z is carboxy substituted alkyl (e.g., $C_1$–$C_6$ alkyl $CO_2R^3$) or

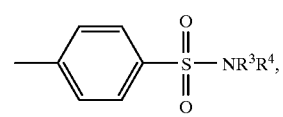

where R³ is hydrogen.
R⁴ in the above formulas is preferably hydrogen.
The invention also provides a pharmaceutical composition comprising a compound of Formula I together with a pharmaceutically acceptable diluent, excipient, or carrier therefor. Especially preferred formulations utilize compounds wherein A is phenyl, especially compounds of the Formula Ia

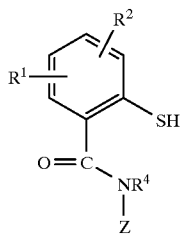

Ia wherein $R^1$, $R^2$, $R^4_1$ and Z are as defined above, and n is 2 and Y is a bond.

Also provided is a method of treating bacterial infections comprising administering an antibacterially effective amount of a compound of Formula I to a subject in need of treatment. Another embodiment of the invention is a method of treating viral infections, including AIDS, comprising administering an antivirally effective amount of a compound of Formula I to a subject in need of treatment. A preferred method utilizes compounds wherein A is phenyl.

DETAILED DESCRIPTION

"$C_1$–$C_6$ alkyl" means a straight or branched aliphatic group having from 1 to 6 carbon atoms. Examples include methyl, ethyl, isobutyl, n-pentyl, and isohexyl.

The term "O-$C_1$–$C_6$ alkyl" means the foregoing alkyl radicals bonded through oxygen, examples of which include methoxy, ethoxy, isopropoxy, tert-butoxy, and the like. Typical "$C_3$–$C_6$ cycloalkyl" groups include cyclopropyl, cyclopentyl, cyclohexyl, and the like.

"Het" is a cyclic or bicyclic ring having from 4 to 10 atoms, from one to four of which are selected from O, S, or N. Het includes non-aromatic groups such as morpholino and pyrrolidino. Preferred Het groups are 5- or 6-membered mono-cyclic aromatic rings having 1 or 2 heteroatoms. Het includes bicyclic rings such as benzofuran, isothiazolone, indole, and the like. Typical groups represented by Het include

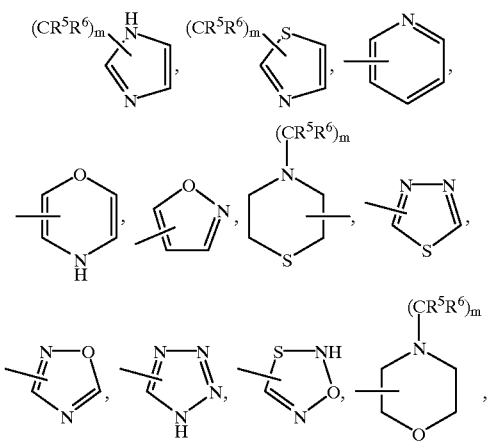

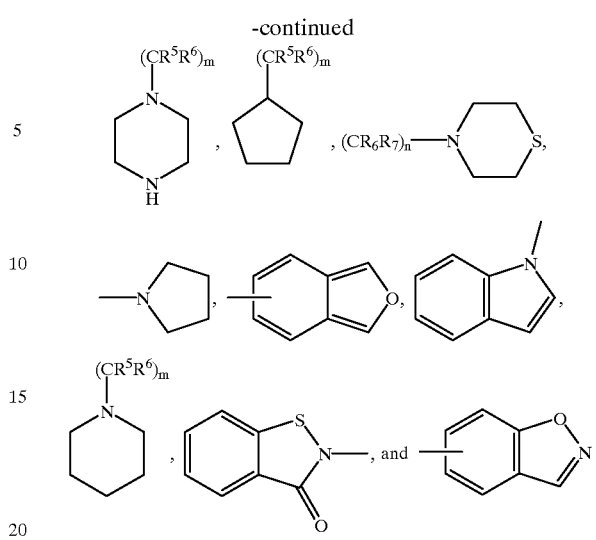

and the like. Other typically preferred Het groups include pyrimidine, pyridazine, pyrazine, oxazole, pyrazole, thiazole, and the like.

As noted above, the alkyl, cycloalkyl, phenyl and Het groups which are included in the definitions of $R^1$, $R^2$, $R^3$, $R^4$, and $R^5$ can be substituted with 1 to 3 groups selected from halo, hydroxy, cyano, nitro, $NR^3COR^4$, $CO^2R^3$,

$NR^3R^4$, $CONR^3R^4$, $S(O)_mR^3$, $PO_4(R^3)_3$, $S(O)_mNR^3R^4$, and $COR^3$, where m, $R^3$, and $R^4$ are as defined above. Typical substituted alkyl groups thus include chloromethyl, 3-bromopropyl, trifluoromethyl, 4-hydroxyhexyl, 1-carboxy-2-methylbutyl, 3-methylthiobutyl, 4-methylsulfonylbutyl, dimethylaminomethyl, 2,3-dibromobutyl, 2-amino-3-chloro-4-carboxybutyl, 3-acetomidopropyl, 2-acetylethyl, 2-methoxycarbonylethyl, 1,1-diacetylpropyl, and the like.

Preferred substituted alkyl groups are those having 1, 2, or 3 substituents selected from halo, hydroxy, and carboxy. Such preferred groups include 1-bromo-2-hydroxypropyl, 1,1-dimethyl-3-hydroxypropyl, 1-hydroxymethyl-2-fluoromethyl-3-carboxybutyl, 1-carboxy-2-methylbutyl, 1-carboxy-3-methylbutyl, 1,2,3-trihydroxypentyl, and the like.

Typical substituted cycloalkyl groups include 2-fluorocyclopropyl, 2,2-dibromocyclopropyl, 2-carboxycyclobutyl, 2-aminosulfonylcyclopentyl, 2-amino-3-carboxycyclopentyl, and 3-isopropylsulfinylcyclohexyl.

In the above formulas, $R^1$ and $R^2$ can be halo, which term includes fluoro, chloro, bromo, and iodo. $R^1$, $R^2$, and Z can include the group phenyl-$(CR^5R^6)_m$— in which the phenyl can be unsubstituted or substituted with groups including halo, hydroxy, cyano, nitro, $NR^3R^4$, $NR^3COR^4$, $CO_2R^3$, $CONR^3R^4$, $S(O)_mR^3$, $S(O)_mNR^3R^4$, and $COR^3$. Typical $NR^3R^4$ substituents include amino, methylamino, dimethylamino, ethyl-isohexylamino, cyclopropylamino, N-acetylamino, N-methyl-N-acetylamino, benzylamino, and 3-chlorobenzylamino.

Typical substituents defined by $NR^3COR^4$ include cyclopropylcarbonylamino, N-isobutyl-N-cyclohexyl carbonylamino, and the like. Typical groups defined by $CO_2R^3$ include the free carboxy acid when $R^3$ is hydrogen, and esters such as $C_1$–$C_6$ alkyl esters, benzyl esters, cyclobutyl esters, and the like. Amide substituents are defined by $CONR^3R^4$, and include carboxamide, N-methyl-carboxamide, and N,N-diethyl-carboxamide. Typical $S(O)_m R^3$ substituent groups include methylthio, ethylsulfinyl, cyclopropylsulfonyl, and the like. Sulfonamide substituents include N-methylsulfonamide, N,N-dimethylsulfonamide, and the like. Typical phenyl-$(CR^5R^6)_m$— groups substituted with the foregoing substituent groups thus include:

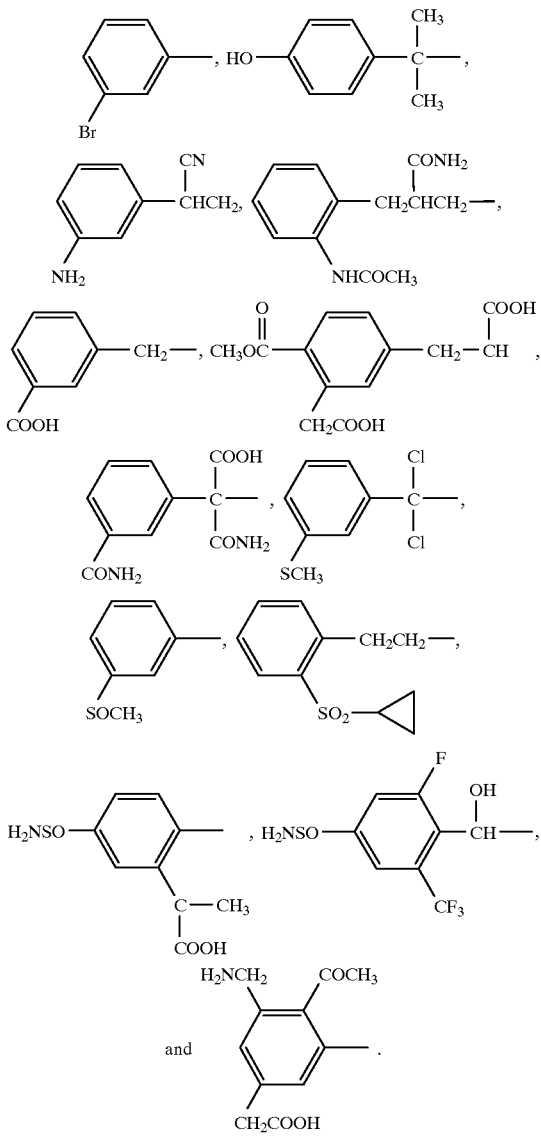

Typical substituted Het-$(CR^5R^6)_m$— include:

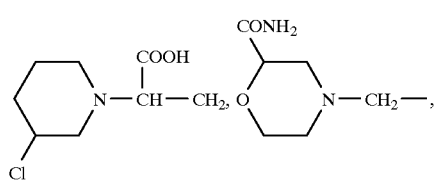

In the invention compounds of Formula I, A can be monocyclic or polycyclic. Preferred A rings are monocyclic 6-membered rings, optionally containing 1 or 2 heteroatoms selected from O, S, and N, most preferably N. Typical ring systems defined by A include the following preferred structures, where Y is hydrogen when n is 1, and Y is a bond when n is 2.

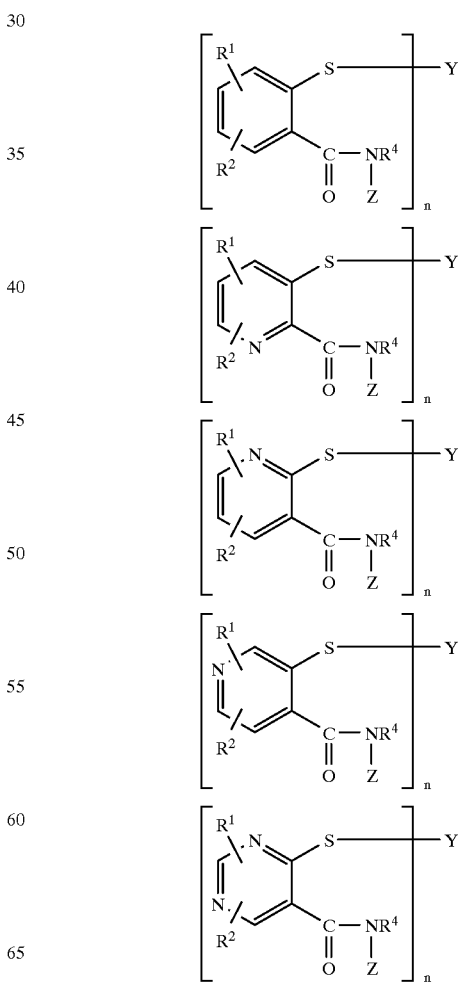

-continued
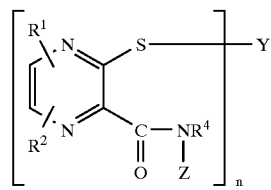
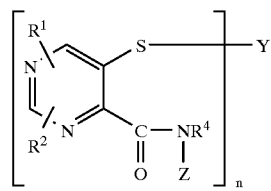
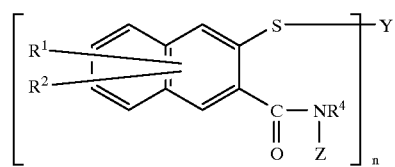
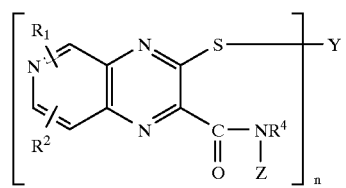
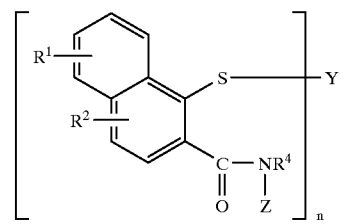
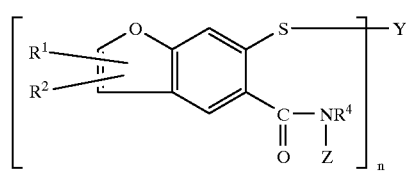
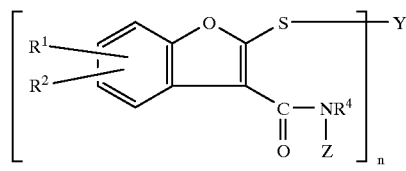
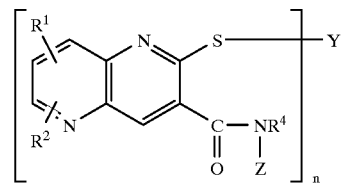
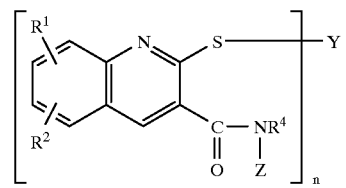
-continued
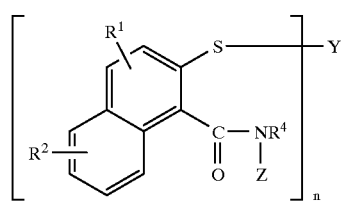
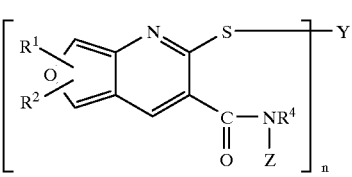
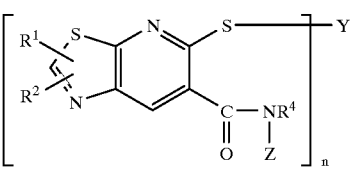
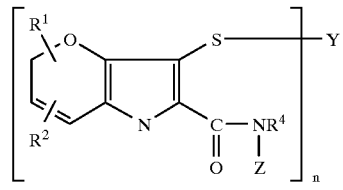
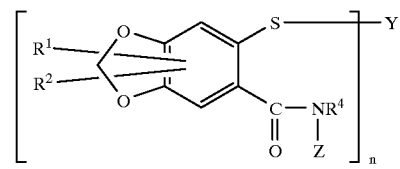
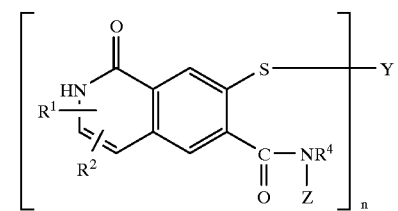
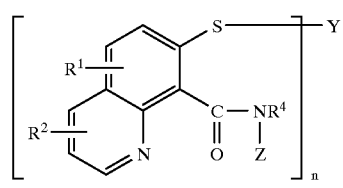
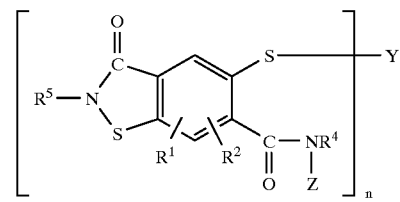

-continued

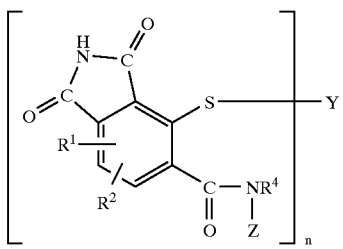

As noted above, a preferred embodiment of the invention includes thiobenzamides of Formula IIa

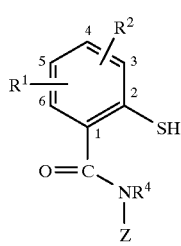

Typical compounds defined within this embodiment are those listed below.

| $R^1$ | $R^2$ | $R^4$ | Z |
| --- | --- | --- | --- |
| 5-OH | H | H | H |
| 4-$NO_2$ | 3-$CH_3$ | H | $CH_3$ |
| 3-$NH_2$ | 6-isopropyl | H | cyclopropyl |
| 6-fluoro | 3-chloro | —$CH_3$ | 2-methylcyclohexyl |
| 5-isobutoxy | H | —Et | 3-carboxypentyl |
| 4-methylamine | 3-ethyl | H | 3-aminopropyl |
| 5-acetamido | H | —iPr | 4-aminosulfonylphenyl |
| 4-carboxy | H | H | 4-dimethylamino-sulfonylphenyl |
| 4-carboxy | H | H | 2-dimethylamino-sulfonylphenyl |

Another preferred embodiment of the invention are dithiobisbenzamides of Formula IIIa

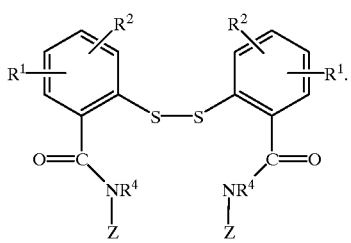

Typical examples include the following:

| $R^1$ | $R^2$ | $R_4$ | Z |
| --- | --- | --- | --- |
| 3-bromo | H | H | H |
| 4-nitro | 6-chloro | H | H |
| 5-amino | 3-methyl | —$CH_3$ | 3-methylpentyl |
| 5-formamido | 3-nitro | H | 3-carboxypenyl |
| 5-acetamido | H | H | H |
| 6-ethoxy | 4-fluoro | H | cyclobutyl |
| 3-isobutyl | H | —Et | methoxycarbonyl methyl |
| 3-isobutyl | H | H | 3-dimethyl amino-sulfonyl phenyl |

Especially preferred compounds of the invention are those of Formula II and Formula III where Z is

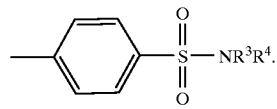

Examples of such compounds include the following:

| $R^1$ | $R^2$ | $R^3$ | $R^4$ |
| --- | --- | --- | --- |
| H | H | H | acetyl |
| 3-isobutyl | H | H | methyl |
| 4-iodo | H | H | n-hexyl |
| 4-amino | 6-chloro | methyl | n-hexyl |
| 5-butyrylamino | 3-methyl | H | acetyl |
| 6-ethyl | H | H | formyl |
| 3-isopropoxy | 6-amino | methyl | propionyl |

The arylthio compounds of the invention can be prepared utilizing any of a number of synthetic processes familiar to those skilled in the art of organic chemistry. Typically, a thiol substituted aryl carboxylic or sulfonic acid can be converted to a dithiobisaryl carboxylic or sulfonic acid by reaction with an oxidant such as hydrogen peroxide or iodine. The dithiobisaryl carboxylic and sulfonic acids can be reacted directly with an amine in the presence of a peptide coupling reagent such as dicyclohexylcarbodiimide (DCC) or 2-ethoxy-1-ethoxycarbonyl-1,2-dihydroquinoline (EEDQ), generally in a mutual unreactive solvent such as dichloromethane or chloroform, to provide dithiobisaryl carboxamides and sulfonamides of the invention. The foregoing reactions are illustrated by the following general scheme:

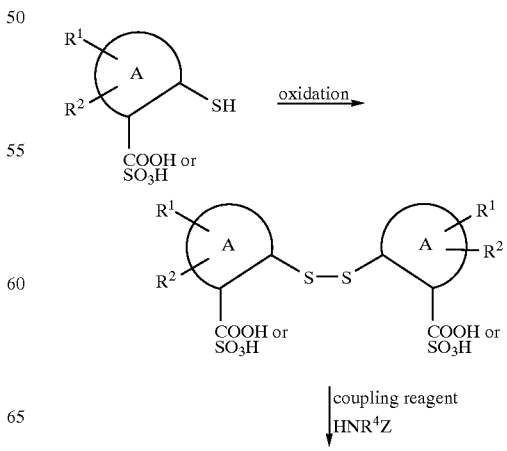

-continued

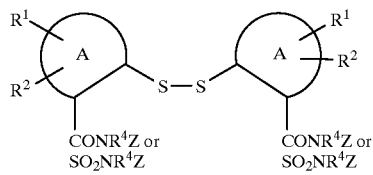

where $R^1$, $R^2$, A, $R^4$, and Z are as defined above.

The carboxamides and sulfonamides can alternatively be prepared by reacting an amine with the corresponding acid halide. The dithiobisaryl carboxylic and sulfonic acids are readily converted to the corresponding acid halides, for example acid chlorides, by reaction with a chlorinating agent such as thionyl chloride or oxalyl chloride. The acid chlorides are readily converted to the dithiobisarylamides of the invention by reaction with an amine, for instance as illustrated by the following scheme:

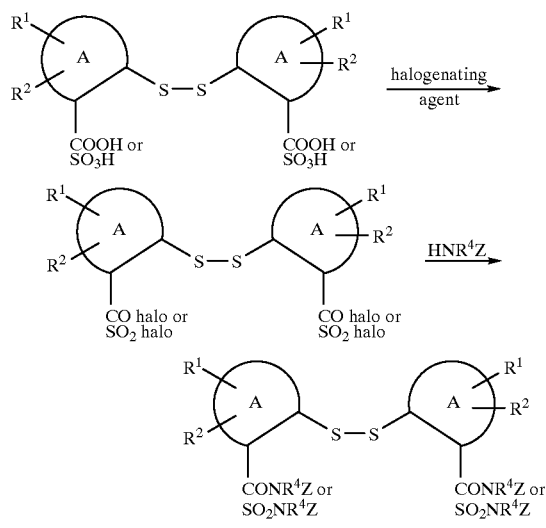

where $R^1$, $R^2$, A, $R^4$, and Z are as defined above.

The amide formation reaction generally is accomplished by reacting two molar equivalents of the is amine $ZNHR^4$ with one molar equivalent of the dithiobisaroyl chloride. The reactants normally are mixed in a mutual solvent such as dichloromethane, acetone, toluene or the like, and the reaction generally is substantially complete within 2 to 6 hours when carried out at a temperature of about 0° to 100° C. A mild base such as triethylamine or pyridine can be added to act as acid scavenger if desired. The product is readily isolated by removing the solvent, and generally, the product can be purified, if needed, by crystallization or the like.

The dithiobisarylamides so prepared are readily converted to the thioarylamides of the invention by reaction with a reducing agent such as 1,4-dithiothreitol, according to the following scheme:

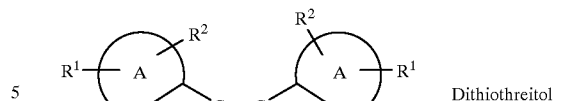

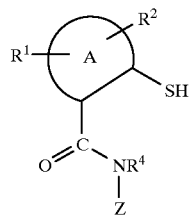

where $R^1$, $R^2$, and $R^4$ and Z are as defined above. The hydrolysis reaction typically is carried out in a mutual solvent such as ethanol or acetone, and normally is complete within 0.5 to 2 hours when conducted at a temperature of about 50 to about 50° C. The product thiol is readily isolated by removing the solvent and crystallizing the product.

An alternative method for preparing the dithiobisarylamides of the invention comprises reacting a 2-halo arylamide with elemental sulfur and sodium monosulfide according to the scheme

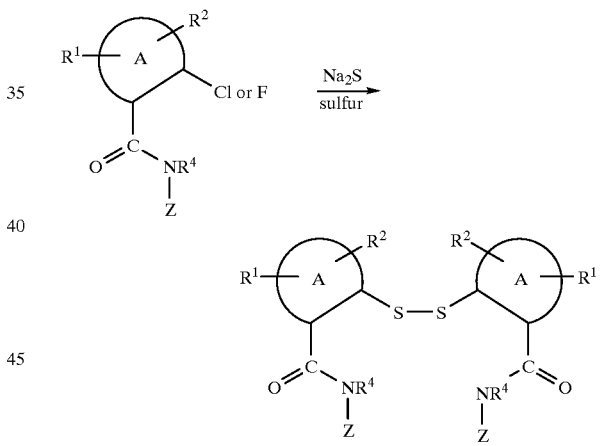

The reaction typically is carried out in a mutual solvent such as methanol or ethanol, and generally is substantially complete within 1 to 2 hours when carried out at a temperature of about 25° to about 100° C. The dithiobisarylamide is readily isolated by removing the reaction solvent and crystallizing the product from a solvent such as isopropanol or the like.

The dithiobisaryl ketones and oximes (i.e., Formula I where X is

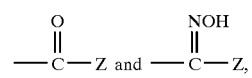

respectively) can be prepared by first reacting an aryl thiol with a strong base such as n-butyl lithium to produce an ortho lithio aryl thiol, and reacting the lithiated intermediate with an N-alkyl-N-alkoxy amide. The reaction is depicted by the following scheme:

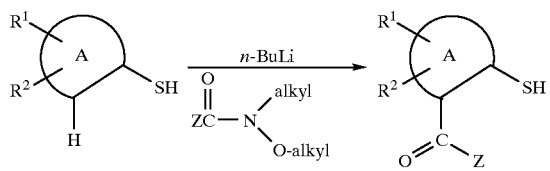

The arylthiol generally is reacted with about two molar equivalents of n-butyl lithium, normally at a reduced temperature of about −40 to 0° C., in an unreactive organic solvent such as diethyl ether, tetrahydrofuran, or hexane. The lithiated aryl thiol reacts with the N-alkyl-N-alkoxy amide (e.g., an N-methyl-N-methoxy benzamide) to form the thiol substituted aryl ketone. The aryl ketone can be reacted with hydroxylamine to form the corresponding oxime, or it can be converted to the corresponding dithiobisaryl ketone by reaction with about an equimolar amount of diethylazodicarboxylate

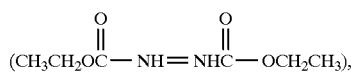

generally in an unreactive solvent such as dichloromethane. The dithiobisaryl ketone, compounds of the formula

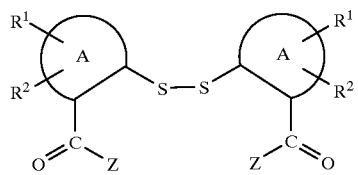

are readily converted to the corresponding oximes by reaction with hydroxylamine, generally in an organic solvent such as ethanol or the like. Bases such as pyridine or triethylamine can be utilized if desired to act as acid scavengers.

In the above reactions, if the $R^1$ and $R^2$ substituents themselves are reactive, for example if $R^1$ is OH, COOH, or $NH_2$, the substituents can themselves be protected according to techniques known in the art to prevent unwanted side reactions. For example, the reactive groups can be converted to a derivative which will protect the substituent from unwanted side reactions, and which can subsequently be removed to regenerate the original substituent group. A variety of protecting groups known in the art may be employed. For example, typical hydroxy protecting groups include substituent groups which can be added to a hydroxy, and then readily removed when desired. Such groups include acyl groups such as formyl and acetyl, as well as benzyl, trimethylsilyl, and the like. Amino groups also may need protection, and typical amino protecting groups include acyl groups such as acetyl, pivaloyl, and tert-butoxycarbonyl (BOC), and arylalkyl groups such as p-nitrobenzyl and the like. Carboxylic acid groups generally are converted to esters such as tert-butyl and 2,2,2-trichloroethyl, all of which can be readily removed when desired, for example, by hydrolysis in the presence of an acid such as hydrochloric acid or trifluoroacetic acid. Examples of many of these typical protecting groups may be found in "Protective Groups in Organic Synthesis" by T. W. Greene and P. Wuts, John Wiley & Sons, 1991.

As noted above, a particularly preferred group of compounds are those of Formula I where X is

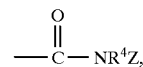

and Z is an alkyl group substituted by at least one carboxy group. An especially preferred method for preparing such compounds is to react a dithiobisaroyl halide with an amino acid. Typical amino acids which can be utilized are those α-amino acids which are common constituents of proteins, for example glysine, alanine, valine, leucine, isoleucine, phenylalanine, serine, threonine, lysine, δ-hydroxylysine, arginine, aspartic acid, asparogine, glutamic acid, glutamine, and the like. A typical synthesis is depicted as follows:

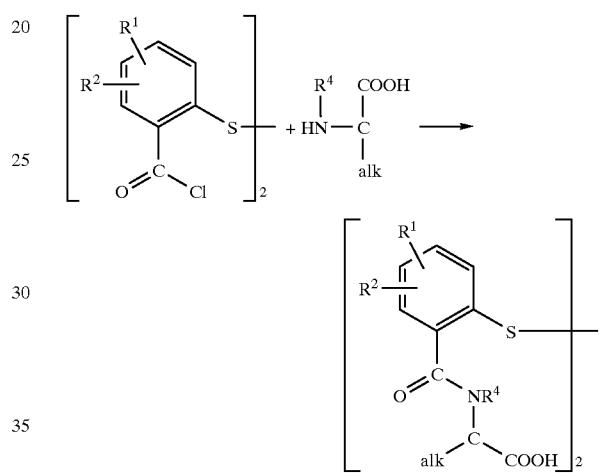

where $R^1$ and $R^2$ are as defined above, and alk is a lower alkyl residue which may be substituted with groups such as carboxy, hydroxy, amino, carboxamide, and the like. The carboxy groups typically are protected by conversion to esters during the reaction, for instance, tert-butyl, benzyl or the like, which groups can be readily hydrolyzed after the reaction to give the free acids.

Non-symmetrical compounds of Formula I, i.e., compounds of the formula

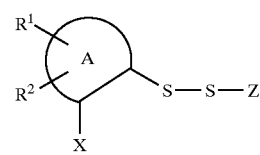

can be prepared by reacting a thiol of the formula HS-$Z^1$ with an isothiazolone according to the following scheme:

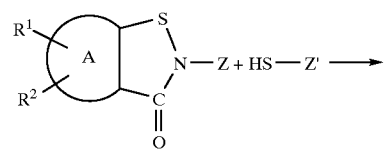

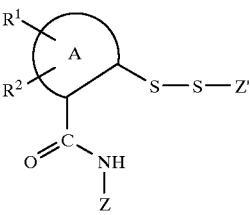

where $R^1$, $R^2$, A, and Z are as defined above, and $Z^1$ is one of the groups defined by Z, but Z and $Z^1$ in the above product do not have to be the same group. For example, the following specific reaction can be carried out:

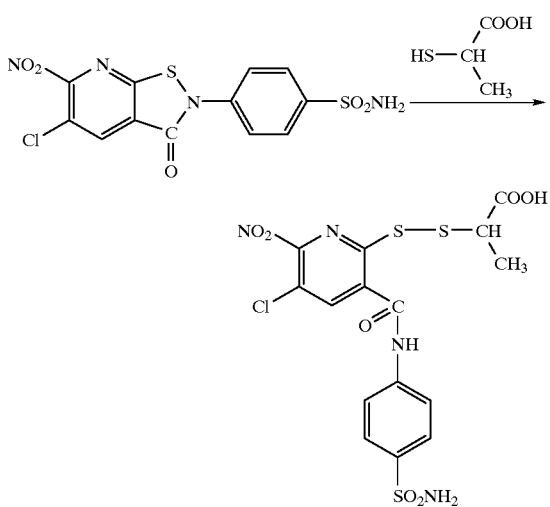

The reaction of an isothiazolone and a thiol generally is accomplished by mixing approximately equimolar quantities of the reactants in a mutual solvent such as methanol, toluene, xylene, or the like, and heating the mixture to about 30° C. to about 100° C. for 8 to 24 hours. The product is isolated by removing the solvent, and it can be further purified by crystallization or chromatography. The isothiazolones utilized in the above reaction are readily available by simply reacting a dithiobisarylamide of the invention with an oxidizing agent such as chlorine or bromine, or a halocarbonylsulfenyl halide, for example according to the following scheme:

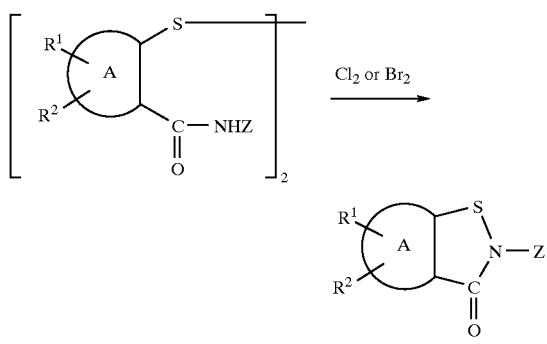

Some of the reactions described above may result in mixtures of isomers. For example, some of the compounds contain one or more asymmetric carbon atoms, and as such can exist as stereochemical isomers. The mixtures can be separated, if desired, into the pure isomers by methods known to those skilled in the art, e.g., by fractional distillation, crystallization, and/or chromatography. Alternatively, specific isomers can be prepared utilizing a stereospecific synthesis, for instance by utilizing an optically active α-aminoacid (e.g., L-leucine or L-aspartic acid) to react with a dithiobisaroyl halide.

Certain of the compounds of this invention can form salts and solvates. For example, compounds wherein $R^1$ or $R^2$ is an amino group can react with inorganic and organic acids to form acid addition salts. Typical acids commonly employed include hydrochloric, sulfuric, acetic, malonic, paratolenesulfonlc, and the like. Compounds which have an acidic group, for instance when Z contains a free carboxy group, can react with organic and inorganic bases to form salts. Typical bases include sodium hydroxide, triethylamine, pyridine, potassium carbonate, and the like.

Solvates are generally formed when crystallizing the invention compounds from solvents such as water, ethanol, isopropanol, and the like.

The synthesis of the compounds of this invention is further illustrated by the following detailed examples. The examples are not to be construed as limiting the invention in any respect. The starting materials utilized in the examples are readily available from commercial sources, or can be prepared by methodologies reported in the scientific literature. For example, Bell P., *J. Am. Chem. Soc.*, 1942:2905, describes a series of benzamides which can be utilized. Methods reported by M. L. Carmellino, et al., *Eur. J. Med. Chem.*, 1994;29:743–751, provide fluorinated-thiobenzoic acid derivatives which can be utilized. Methods reported by O. Francis Bennett, et al., *Organic Prep. and Proced. Int.*, 1974;6(6):287–293, provide a series of alkoxy-thio-benzoic acid derivatives. Methods reported by T. Vitali, et al., *Il Farmaco Ed. Sc.*, 1968;23:468–476, give alkyl-thio-benzoic acid derivatives which can be utilized.

PREPARATION A 2,2'-Dithiobisbenzoyl chloride

A mixture of 2,2'-dithiobisbenzoic acid (25 g, 81.6 mmol) in 350 mL of thionyl chloride was heated at reflux for 18 hours. The resulting solution was cooled to about 30° C. and excess thionyl chloride was removed in vacuo. The crude solid was slurried in hexane and the title compound was recovered by filtration to yield 21.2 g. This compound was used without further purification, mp 150–151° C.;

NMR (CDCl$_3$): δ 8.4 (m, 2H), 7.7 (d, 2H), 7.5 (m, 2H), 7.3–7.4 (m, 2H).

PREPARATION B 2,2'-Dithiobisr[3-fluorobenzoyl chloridel

A mixture of 2,2'-dithiobis[3-fluorobenzoic acid] (0.4 g, 1.0 mmol) and thionyl chloride (10 mL) was reacted according to the procedure described in Preparation A to yield 0.3 g of 2,2'-dithiobis[3-fluorobenzoyl chloride]. This compound was used without further purification.

PREPARATION C 2,2'-Dithiobis[4-fluorobenzoyl chloride]

A mixture of 2,2'-dithiobis[4-fluorobenzoic acid] (5.0 g, 14.6 mmol) and thionyl chloride was reacted according to the procedure described in Preparation A to yield 4.1 g of 2,2'-dithiobis[4-fluorobenzoyl chloride]. The compound was used without further purification.

PREPARATION D 2,2'-Dithiobis[5 -fluorobenzoyl chloride]

A mixture of 2,2'-dithiobis[5-fluorobenzoic acid] (5.0 g, 14.6 mmol) and thionyl chloride (40 mL) was reacted according to the procedure described in Preparation A to yield 4.9 g of 2,2'-dithiobis[5-fluorobenzoyl chloride]. This compound was used without further purification.

PREPARATION E
2,2'-Dithiobis[3-methoxybenzoyl chloride]

A mixture of 2,2'-dithiobis[3-methoxybenzoic acid] (2.0 g, 5.0 mmol) and thionyl chloride (30 mL) was reacted according to the procedure described in Preparation A to yield 1.9 g of 2,2'-dithiobis[3-methoxybenzoyl chloride]. This compound was used without further purification.

PREPARATION F
2,2'-Dithiobis[4-methoxybenzoyl chloride]

A mixture of 2,2'-dithiobis[4-methoxybenzoic acid] (2.2 g, 6.6 mnmol) and thionyl chloride (20 mL) was reacted according to the procedure described in Preparation A to yield 2.1 g of 2,2'-dithiobis[4-methoxybenzoyl chloride]. This compound was used without further purification.

PREPARATION G
2,2'-Dithiobis[5-methoxybenzoyl chloride]

A mixture of 2,2'-dithiobis[5-methoxybenzoic acid] (0.8 g, 2.0 mmol) and thionyl chloride (10 mL) was reacted according to the procedure described in Preparation A to yield 0.8 g of 2,2'-dithiobis[5-methoxybenzoyl chloride]. This compound was used without further purification.

PREPARATION H
2,2'-Dithiobis[3-methylbenzoyl chloride]

A mixture of 2,2'-dithiobis[3-methylbenzoic acid] (2.9 g, 8.6 mnmol) and thionyl chloride (40 mL) was reacted according to the procedure described in Preparation A to yield 2.6 g of 2,2'-dithiobis[3-methylbenzoyl chloride]. This compound was used without further purification.

PREPARATION I
2,2'-Dithiobis[4-methylbenzovl chloride]

A mixture of 2,2'-dithiobis[4-methylbenzoic acid] (3.8 g, 11.9 mmol) and thionyl chloride (50 mL) was reacted according to the procedure described in Preparation A to yield 3.6 g of 2,2'-dithiobis[4-methylbenzoyl chloride]. The compound was used without further purification.

PREPARATION J
2,2'-Dithiobis[5-methylbenzoyl chloride]

A mixture of 2,2'-dithiobis[5-methylbenzoic acid] (0.6 g, 1.8 mmol) and thionyl chloride (10 mL) was reacted according to the procedure described in Preparation A to yield 0.3 g of 2,2'-dithiobis[5-methylbenzoyl chloride]. The compound was used without further purification.

PREPARATION K
2,2'-Dithiobis[6-methylbenzoyl chloride]

A mixture of 2,2'-dithiobis[6-methylbenzoic acid] (0.6 g, 1.8 mmol) and thionyl chloride (10 mL) was reacted according to the procedure described in Preparation A to yield 0.3 g of 2,2'-dithiobis[6-methylbenzoyl chloride]. The compound was used without further purification.

PREPARATION L
2,2'-Dithiobis[3-pyridinecarbonyl chloride]

A mixture 2,2'-dithiobis[3-pyridinecarboxylic acid] (1.5 g, 4.8 mmol) and thionyl chloride (20 mL) was reacted according to the procedure described in Preparation A to yield 1.3 g of 2,2'-dithiobis[3-pyridinecarbonyl chloride]. The compound was used without further purification.

PREPARATION M
4-(3-Oxo-3H-benzo[d]isothiazol-2-yl)benzenesulfonamide

A solution of 60 mL of methanol and 60 mL of tetrahydrofuran was cooled to 0° C. and treated dropwise with 3.9 g (30.0 mmol) of chlorocarbonylsulfenyl chloride. The mixture was stirred at 0° C. for 20 minutes and treated with 9.0 g (29.2 mmol) of 2-thio-N-(4-sulfamoylphenyl)benzamide (Example 6). The reaction was stirred at 0° C. for 0.5 hours and allowed to come to room temperature over 18 hours. The suspension was diluted with 200 mL of ether, stirred for 1 hour and the solid removed by filtration. After washing with ether, the solid was dried in vacuo to give 7.8 g of the title compound. An additional 2.2 g was obtained by concentrating the mother liquors and triturating the residue with ether. The mp of both fractions was 283–285° C.

PREPARATION N
[s-(R*,R*)]-3-Methyl-2-(3-oxo-3H-benzo[d]isothiazol-2-yl)pentanoic acid A stirred, room temperature suspension of 5.3 g (10.0 mmol) of [S-(R*,R*)]-2-[2-[2-(1-carboxy-2-methylbutylcarbamoyl)phenyldisulfanyl benzoylamino]-3-methylpentanoic acid (prepared by the general method of Example 5) in 200 mL of dichloromethane was treated dropwise with 2.4 g (15.0 mmol) of liquid bromine. The reaction mixture was stirred at room temperature for 2 hours, and the solvent was evaporated in vacuo. The residue was triturated with dichloromethane, which was also evaporated in vacuo to remove excess bromine. The residue was partitioned between dichloromethane/5% sodium bicarbonate (200 mL each). The aqueous layer was separated, washed with dichloromethane, and acidified to pH 1.5 with 6.0M hydrochloric acid. After extracting with dichloromethane (2×75 mL), the combined organic layers were washed with water, dried ($MgSO_4$), filtered and evaporated in vacuo to give 4.8 g of the title compound, mp 50–52° C.

PREPARATION O
2-Mercaptobenzophenone

To a solution of N,N,N',N'-tetramethylethylene diamine (4.4 g, 0.038 mol) and thiophenol (2 g, 0.018 mol) in cyclohexane (40 mL) was added dropwise n-butyllithium (24 mL, 0.038 mol) at room temperature. The suspension was stirred under nitrogen for 16 hours, followed by the dropwise addition of N-methoxy-N-methylbenzamide (3.3 g, 0.019 mol). After stirring for 20 minutes, the reaction mixture was added to cold aqueous HCl (1N). The product was partitioned between ethyl acetate and the acidic solution. The layers were separated and the organic portion was washed with brine, dried ($Na_2SO_4$), filtered, and the filtrate was concentrated in vacuo. The liquid obtained was purified using silica gel chromatography (75% hexane/25% ethyl acetate) to give 2.3 g of the title compound a as a viscous yellow liquid.

NMR ($CDCl_3$) δ 7.8–7.2 (m, 9H), 4.2 (s, 1H) ppm.

PREPARATION P
2-Mercapto-5-chloro-benzenesulfonamide

To 34.0 g (0.15 mol) of 2,5-dichloro-benzene sulfonamide in 200 mL of DMF was added 16.0 g (0.28 mol) of sodium hydrogensulfide. The mixture was refluxed for 18 hours, then cooled, concentrated, and the solids collected by filtration. The solids were dissolved in hot water, the pH adjusted to 4.0 and the precipitate filtered. This material was dried to yield 10.1 g of the title compound, mp 142–144° C.

PREPARATION Q

2-Chloro-5-nitrobenzamide

A mixture of 2-chloro-5-nitrobenzoic acid (15.0 g, 74.0 mmol) in 200 mL of dichloromethane was reacted at 24° C. with oxalyl chloride (16.2 mL, 186.0 mmol) and a catalytic amount of dimethylformamide. After 3 hours, the solvent was removed in vacuo, and the residue was redissolved in 200 mL of fresh dichloromethane. The solution was cooled to 0° C., and ammonia was bubbled into the solution for 5 minutes, whereupon the product precipitated from solution. The product was collected by filtration to yield 6.8 g of 2-chloro-5-nitro benzamide, mp 174–175° C.;

NMR (DMSO-$d_6$): δ 8.2 (m, 2H), 8.2 (s, 1H), 7.8–7.9 (m, 2H).

EXAMPLE 1

2,2'-Dithiobis-4'-[sulfamoylbenzanilide] (General method)

A solution of 2,2'-dithiobisbenzoyl chloride (5.0 g, 14.0 mmol) in 50 mL of dichloromethane was added dropwise to a solution of 4-(aminosulfonyl)-aniline (6.2 g, 36.0 mmol) in 125 mL of pyridine cooled to 0° C. The mixture was stirred for 18 hours at 0° C., and the resulting solid was removed by filtration, washed with 1N HCl, water, and dried in vacuo to yield 7.6 g of crude product. This crude material (6.5 g) was suspended in 50 mL dimethylformamide/60 mL ethanol, filtered, and precipitated from the filtered solution by the addition of 10 mL 4% aqueous NaHCO$_3$. The product was collected by filtration, washed with ethanol and water to yield 4.3 g of the title compound, mp 311–312° C.;

NMR (DMSO-$d_6$): δ 10.9 (s, 2H), 7.7–8.0 (m, 12H), 7.5 (m, 2H), 7.4 (m, 2H), 7.3 (s, 4H).

EXAMPLE 2

2,2'-Dithiobis-N-[4-[(methylamino)sulfonyl]phenyl]-benzamide

This compound was prepared according to the general method of Example 1 using 2,2'-dithiobisbenzoyl chloride (2.2 g, 6.0 mmol) in 15 mL of dichloromethane and 4-[(methylamino)sulfonyl]aniline (3.0 g, 16.0 mmol) in 20 mL of pyridine. The crude product was recrystallized from dimethylformamide, ethanol, and 4% aqueous NaHCO$_3$ to afford 1.9 g of the title compound, mp 245–247° C.;

NMR (DMSO-$d_6$): δ 10.9 (s, 2H), 7.9 (m, 4H), 7.7–7.8 (m, 8H), 7.5 (m, 2H), 7.3–7.4 (m, 6H), 2.4 (m, 6H)

EXAMPLE 3

2,2'-Dithiobis-N-[4[[(1-methylethyl)amino]sulfonyl]-phenyl]benzamide

This compound was prepared according to the general method of Example 1 using 2,2'-dithiobisbenzoyl chloride (1.3 g, 3.0 mmol) in 30 mL of dichloromethane and 4-[(1-methylethylamino)sulfonyl]aniline in 30 mL pyridine. The crude product was recrystallized from dimethylformamide, ethanol, and water to yield 0.7 g of the title compound, mp 146–148° C.; NMR (DMSO-$d_6$): δ 10.9 (s, 2H), 7.9 (d, 4H), 7.7–7.8 (m, 8H), 7.5 (m, 4H), 7.4 (m, 2H), 3.2 (m, 2H), 0.9 (d, 12H).

EXAMPLE 4

2,2'-Dithiobis-N-[4-[(acetylamino)sulfonyl]phenyl]-benzamide

The compound was prepared according to the general method of Example 1 using 2,2'-dithiobisbenzoyl chloride (3.0 g, 8.0 mmol) in 30 mL of dichloromethane and 4-[(acetylamino)sulfonyl]aniline (5.6 g, 26.0 mmol) in 100 mL of pyridine. The crude product was purified by chromatography on a silica gel column using chloroform/methanol (1:1 v/v) as the mobile phase. The pure fractions were pooled, concentrated in vacuo to provide a solid, which was then recrystallized from ethanol/water (1:1 v/v) to yield 0.5 g of 2,2'-dithiobis-N-[4-[(acetylamino)sufonyl]phenyl)-benzamide, mp 180–182° C.;

NMR (DMSO-$d_6$): δ 12.0 (b, 2H), 11.0 (s, 2H), 7.8–8.0 (m, 16H), 7.5 (m, 2H), 7.4 (m, 2H), 1.9 (s, 6H).

EXAMPLE 5

2-[[2-[(1-Carboxy-2-methylbutylcarbamoyl)phenyl disulfanyl]-benzoyl]-amino]-3-methylpentanoic acid Racemic iso-leucine (26.2 g, 0.2 mol) was slurried in 100 mL of absolute ethanol and treated with a solution of sodium (4.6 g, 0.2 mol) in 100 mL of ethanol, then cooled to −50° C. 2,2'-Dithiobisbenzoyl chloride (17.2 g, 0.5 mol) was added portionwise and the solution was stirred for 18 hours. The solvent was removed in vacuo and the solid was dissolved in water and filtered to remove any insoluble material. The compound was precipitated from the filtrate with the addition of 1N HCl to a final pH=3 and collected by filtration. The product was again dissolved in water using NaHCO$_3$, treated with charcoal, filtered, and precipitated with the addition of 1N HCl to pH=3. This procedure was repeated again to yield 8.9 g of the title compound. The compound was recrystallized from 60% aqueous ethanol to afford 1.3 g of the title compound, mp 216–218° C.;

NMR (DMSO-$d_6$): δ 12.7 (s, 2H), 8.6–8.8 (m, 2H), 7.6 (m, 4H), 7.4 (m, 2H), 7.3 (m, 2H), 4.3–4.6 (m, 2H), 2.0 (m, 2H), 1.5 (m, 2H), 1.3 (m, 1H), 0.9 (m, 12H).

EXAMPLE 6

2-Thio-N-(4-sulfamoylphenyl)benzamide 2,2'-Dithiobis(4'-sulfamoyl)benzanilide (0.1 g, 0.2 mmol) was dissolved in 4 mL of dimethylformamide and 1.6 mL of 2.7% NaH$_2$PO$_4$. Dithiothreitol (0.1 g, 0.7 mmol) was added, and the mixture was allowed to stir for 0.5 hours. Formic acid (10 mL 10% aqueous) was added to precipitate the product, which was collected by filtration, washed with water and diethyl ether to yield 72 mg of 2-thio-N-(4-sulfamoylphenyl)-benzamide, mp 230–231° C.;

NMR (DMSO-$d_6$): δ 10.7 (s, 1H), 7.9–7.7 (m, 4H), 7.6 (d, 1H), 7.5 (d, 1H), 7.4 (m, 1H), 7.3–7.2 (m, 3H).

EXAMPLE 7

2,2'-Dithiobis-5-nitrobenzamide

2-Chloro-5-nitrobenzamide (6.8 g, 33.0 mmol) was heated to reflux in 90 mL of ethanol and treated portionwise with Na$_2$S.9H$_2$O (2.6 g, 20.5 mmol) and sulfur (0.7 g, 20.5 mmol). The mixture was heated at reflux for 1 hour, then cooled to room temperature, whereupon a solid formed. The solid was removed by filtration to yield 2.6 g of the title compound, mp 266–269° C.;

NMR (DMSO-$d_6$): δ 8.7 (s, 2H), 8.7 (s, 2H), 8.3 (m, 2H), 8.0 (s, 2H), 7.8 (m, 2H).

EXAMPLE 8

2,2'-Dithiobis-5-aminobenzamide 2,2'-Dithiobis-5-nitrobenzamide (2.6 g, 7.0 mmol) from Example 7 was added portionwise to a refluxing slurry of reduced iron (8.7 g) in 65 mL of water containing 0.1 mL of acetic acid. The resulting slurry was heated at reflux for 2 hours, then cooled to room temperature. The slurry was made strongly basic (pH=10) by the addition of 14 mL of 1N NaOH and filtered. Acetic acid was added to the solution to obtain a pH=7. While bubbling oxygen into the solution, a pH=6–7 was maintained with the addition of acetic acid. A solid gradually formed and was filtered to yield 1.1 g of 2,2'-dithiobis-5-aminobenzamide, mp 188–190° C.;

NMR (DMSO-$d_6$): 7.7 (s, 2H), 7.2–7.3 (m, 4H), 6.5–6.6 (m, 4H), 5.3 (s, 4H).

EXAMPLE 9

2,2'-Dithiobis(5-acetylamino)benzamide 2,2'-Dithiobis-5-aminobenzamide (1.1 g, 3.4 mmol) from Example 8 was dissolved in 6 mL of glacial acetic acid on a steam bath and treated with acetic anhydride (0.7 mL, 7.2 mmol). Upon cooling, the product precipitated from solution. An additional 4 mL of glacial acetic acid and 0.1 mL of acetic anhydride was added, and the mixture was heated at reflux for 10 minutes. The mixture was cooled to room temperature. The crude product was recovered by filtration and recrystallized from a mixture of dimethylformamide:dimethyl sulfoxide:water (30:30:40 v/v/v) to yield 0.8 g of 2,2'-dithiobis-(5-acetyl-amino)-benzamide), mp 301–303° C.;

NMR (DMSO-$d_6$): δ 10.1 (s, 2H), 8.0 (s, 2H), 7.8 (s, 2H), 7.5 (s, 6H), 2.0 (s, 6H).

EXAMPLE 10

5-Acetylamino-2-thiobenzamide 2,2'-Dithiobis-5-(acetamidobenzamide) from Example 9 (80 mg, 0.2 mmol) was partially dissolved in 3 mL of dimethylformamide and 1.5 mL 2.7% $NaH_2PO_4$. A homogeneous solution was realized with the addition of dithiothreitol (0.1 g, 0.7 mmol) and after 20 minutes, 10 mL of 100 acetic acid was added. The solvents were removed in vacuo, the residue slurried in water, and the solid removed by filtration to yield 22 mg of the title compound, mp 148–149° C.;

NMR (DMSO-$d_6$): δ 10.0 (s, 1H), 7.9 (s, 1H), 7.7 (s, 1H), 7.5 (m, 2H), 7.3 (d, 1H), 5.2 (s, 1H), 2.0 (s,3H).

EXAMPLE 11

2,2'-Dithiobis[3'-sulfamoylbenzanilide]

This compound was prepared according to the general methods described in Example 1 using 2,2'-dithiobisbenzoyl chloride (3.0 g, 8.7 mmol) in 30 mL dichloromethane and 3-(aminosulfonyl)-aniline (3.7 g, 21.0 mmol) in 50 mL pyridine. The crude product was recrystallized from a mixture of dimethylformamide, ethanol, and water to yield 4.2 g of the title compound, mp 222–225° C.

EXAMPLE 12

2.2'-Dithiobis[N-[[4-(aminosulfonyl)phenyl]methy]-benzamide]

A slurry of 4-(aminomethyl)benzenesulfonamide hydrochloride hydrate (6.5 gf 29 mmol) in 100 mL pyridine was allowed to stir with N-methyl-N-(trimethylsilyl)acetamide (13.4 mL, 83.0 mmol) until a homogenous solution occurred. The solution was cooled to 0° C. to 5° C. and a solution of 2,2'-dithiobisbenzoyl chloride (4.0 g, 16.0 mmol) in 20 mL dichloromethane was added dropwise. The resulting solution was allowed to stir for 18 hours and the dichloromethane was removed in vacuo. The crude product was precipitated with the addition of water and the resulting solid was collected by filtration. The crude product was recrystallized from a mixture of dimethylformamide, ethanol, and water to yield 3.3 g of the title compound, mp 267–269° C.

EXAMPLE 13

2,2'-Dithiobis-N-[4'-[(cyclopropylamino)-sulfonyl] phenyl] benzamide)]

This compound was prepared according to the general methods described in Example 1 using 2,2'-dithiobisbenzoyl chloride (1.3 g, 3.7 mmol) in 10 mL dichloromethane and 4-(cyclopropyl-amino-sulfonyl)aniline (2.0 g, 9.4 mmol) in 30 mL pyridine. The crude product was recrystallized from a mixture of dimethylformamide, ethanol, and water to yield 1.0 g of the title compound, mp 242–245° C.

EXAMPLE 14

2,2'-Dithiobis-N-[4'-[(methoxyamino)-sulfonyl] phenyl] benzamide)]

This compound was prepared according to the general methods described in Example 1 using 2,2'-dithiobisbenzoyl chloride (1.6 g, 4.7 mmol) in 30 mL dichloromethane and 4-(methoxy-amino-sulfonyl)-aniline (2.0 g, 9.9 mmol) in 80 mL dichloromethane and 0.8 mL pyridine. The crude product was washed with water and methanol to yield 2.4 g of the title compound, mp 225–228° C.

EXAMPLE 15

2,2'-Dithiobis[N-[4-[(2-pyrimidinylamino)sulfonyl] phenyl]-benzamide]

This compound was prepared according to the general methods described in Example 1 using 2,2'-dithiobisbenzoyl chloride (3.0 g, 8.7 mmol) in 30 mL dichloromethane and 4-amino-N-(2-pyrimidinyl) benzenesulfonamide (5.3 g, 21.7 mmol) in 100 mL pyridine. The crude product was recrystallized from a mixture of dimethylformamide, ethanol, and water to yield 3.9 g of the title compound, mp 280° C.

EXAMPLE 16

2,2'-Dithiobis[N-[4-(aminosulfonyl)phenyl]-4-fluorobenzamide]

This compound was prepared according to the general procedure described in Example 1 using 2,2'-dithiobis[4-fluorobenzoyl chloride] (2.0 g, 5.2 mmol) in dichloromethane (20 mL) and 4-(aminosulfonyl)-aniline (2.2 g,13.0 mmol) in pyridine (30 mL). The crude product was recrystallized from a mixture of dimethylformamide, ethanol, and water to yield 2.6 g of the title compound, mp 309–310° C.

EXAMPLE 17

2,2'-Dithiobis[N-[4-(aminosulfonyl)phenyl]-5-fluorobenzamide]

This compound was prepared according to the general procedure described in Example 1 using 2,2'-dithiobis[5- fluorobenzoyl chloride] (2.0 g, 5.2 mmol) in dichloromethane (20 mL) and 4(aminosulfonyl)-aniline (2.1 g, 11.6 mmol) in pyridine (20 mL). The crude product was recrystallized from a mixture of dimethylformamide, ethanol, and water to yield 1.7 g of the title compound, mp>300° C.

EXAMPLE 18

2,2'-Dithiobis[N-[4-(aminosulfonyl)phenyl]-3-methoxybenzamide]

This compound was prepared according to the general procedure described in Example 1 using 2,2'-dithiobis[3-methoxybenzoyl chloride] (0.9 g, 2.2 mmol) in 8 ml dichloromethane and 4-(aminosulfonyl)-aniline (1.0 g, 5.8 mmol) in 15 mL pyridine. The crude product was recrystallized from a mixture of dimethylformamide, ethanol, and water to yield 0.3 g of the title compound, mp 188–189° C.

EXAMPLE 19

2,2'-Dithiobis[N-[4-(aminosulfonyl)phenyl]-4-methoxybenzamide]

This compound was prepared according to the general methods described in Example 1 using 2,2'-dithiobis[4-methoxybenzoyl chloride] (1.1 g, 2.7 mmol) in dichloromethane (10 ml) and 4-(aminosulfonyl)-aniline (1.1 g, 6.8 mmol) in pyridine (15 mL). The crude product was recrystallized from dimethylformamide, ethanol, and water to yield 0.8 g of the title compound, mp 315–316° C.

EXAMPLE 20

2,2'-Dithiobis[N-[4-(aminosulfonyl)phenyl]-5-methoxybenzamide]

This compound was prepared according to the general methods described in Example 1 using 2,2'-dithiobis[5-methoxybenzoyl chloride] (0.2 g, 0.4 mmol) in 8 mL dichloromethane and 4-(aminosulfonyl)-aniline (0.2 g, 1.2 mmol) in 10 mL pyridine. The crude product was recrystallized from a mixture of dimethylformamide, ethanol, and water to yield 0.1 g of the title compound, mp 242–243° C.

EXAMPLE 21

2,2'-Dithiobis[N-[4-(aminosulfonyl)phenyl]-3-methylbenzamide]

This compound was prepared according to the general procedure described in Example 1 using 2,2'-dithiobis[3-methylbenzoyl chloride] (0.8 g, 2.3 mmol) in 10 mL dichloromethane and 4-(aminosulfonyl)-aniline (1.0 g, 5.8 mmol) in 15 mL pyridine. The crude product was recrystallized from a mixture of dimethylformamide, ethanol, and water to yield 0.7 g of the title compound, mp 308–309° C.

EXAMPLE 22

2,2'-Dithiobis[N-[4-(aminosulfonyl)phenyl]-4-methylbenzamide]

This compound was prepared according to the general procedure described in Example 1 using 2,2'-dithiobis[4-methylbenzoyl chloride] (2.0 g, 5.5 mmol) in dichloromethane (20 mL) and 4-(aminosulfonyl)-aniline (3.4 g,19.9 mmol) in pyridine (40 mL). The crude product was recrystallized from a mixture of dimethylformamide, ethanol, and water to yield 2.1 g of the title compound, mp 319–320° C.

EXAMPLE 23

2,2'-Dithiobis[N-[4-(aminosulfonyl)phenyl]-5-methyl-benzamide]

This compound was prepared according to the general procedure described in Example 1 using 2,2'-dithiobis[5-methylbenzoyl chloride] (2.0 g, 5.3 mmol) in dichloromethane (20 mL) and 4-(aminosulfonyl)-aniline (2.3 g, 13.3 mmol) in pyridine (30 mL). The crude product was recrystallized from a mixture of dimethylformamide, ethanol, and water to yield 1.8 g of the title compound, mp 307° C.

EXAMPLE 24

2,2'-Dithiobis[N-[4-(aminosulfonyl)phenyl]-6-methylbenzamide]

This compound was prepared according to the general procedure described in Example 1 using 2,2'-dithiobis[6-methylbenzoyl chloride] (1.0 g, 2.6 mmol) in 10 mL dichloromethane and 4-(aminosulfonyl)-aniline (1.2 g, 6.7 mmol) in 15 mL pyridine. The crude product was recrystallized once from a mixture of dimethylformamide, ethanol, and water and then from dimethylsulfoxide and water to yield 42 mg of the title compound, mp 273–275° C.

EXAMPLE 25

2,2'-Dithiobis[N-[4-(aminosulfonyl)phenyl]-3-pyridinecarboxamide]

This compound was prepared according to the general procedure described in Example 1 using 2,2'-dithiobis[3-pyridinecarbonyl chloride] (0.6 g, 1.6 mmol) in 10 mL dichloromethane and 4-(aminosulfonyl)-aniline (0.7 g, 4.1 mmol) in 15 mL pyridine. The crude product was recrystallized from a mixture of dimethylformamide, ethanol, and water to yield 0.1 g of the title compound, mp 280° C.

EXAMPLE 26

[S-(R*,R*)]-2-[2-[2-(1-tert-Butoxycarbonyl-2-methylbutylcarbamoyl)-6-fluoro-phenyldisulfanyl]-3-fluorobenzoylamino]-3-methyl-pentanoic acid tert-butyl ester (General method)

A solution of 2,2'-dithiobis[3-fluorobenzoyl chloride] (0.4 g, 1.0 mmol) in 10 mL dichloromethane was added dropwise to a solution of L-isoleucine tert-butyl ester, monohydrochloride (1.0 g, 4.4 mmol) and N-methyl morpholine (0.5 mL, 4.4 mmol) in 30 mL dichloromethane at 0–5° C. The resulting solution was allowed to stir for 18 hours and then allowed to warm to ambient temperature. The mixture was extracted with 5% citric acid, water, 8% $NaHCO_3$, and brine. The organic layer was dried with $MgSO_4$, filtered, and concentrated in vacuo. The crude product was purified by chromatography (Silica : hexane/ethyl acetate). The pure fractions were pooled and concentrated in vacuo to afford 0.6 g of the title compound.

EXAMPLE 27

[S-(R*,R*)]-2-[2-[2-(1-tert-Butoxycarbonyl-3-methylbutylcarbamoyl)-5-fluoro-phenyldisulfanyl]-4-fluorobenzoylamino]-4-methyl-pentanoic acid tert-butyl ester This compound was prepared according to the procedure described in Example 26 using 2,2'-dithiobis[4- fluorobenzoyl chloride] (2.0 g, 5.7 mmol) in 20 mL dichloromethane and L-leucine tert-butyl ester, monohydrochloride (2.8 g, 12.6 mmol) and N-methyl morpholine (3.0 mL, 27.0 mnmol) in 60 mL dichloromethane. The crude product was recrystallized from ethyl acetate to yield 3.1 g of the title compound.

EXAMPLE 28

[S-(R R*)-2-[2-[2-(1-tert-Butoxycarbonyl-3-methylbutylcarbamoyl)-4-fluoro-phenyldisulfanyl]-5-fluorobenzoylamino]-4-methyl-pentanoic acid tert-butyl ester This compound was prepared according to the procedure described in Example 26 using 2,2'-dithiobis[5-fluorobenzoyl chloride] (2.0 g, 5.2 mmol) in 20 mL dichloromethane, L-leucine tert-butyl ester, monohydrochloride, (2.5 g, 11.4 mmol), and N-methyl morpholine (1.4 mL, 12.5 mmol) in 30 mL dichloromethane. The crude product was recrystallized from ethyl acetate to yield 1.8 g of the title compound.

EXAMPLE 29

[S-(R*,R*)]-2-[2-[2-(1-tert-Butoxycarbonyl-3-methylbutylcarbamoyl)-6-methoxy-phenyldisulfanyl]-3-methoxybenzoylamino]-4-methyl-pentanoic acid tert-butyl ester This compound was prepared according to the procedure described in Example 26 using 2,2'-dithiobis[3-methoxybenzoyl chloride] (2.1 g, 5.4 mmol) in 10 mL dichloromethane and L-leucine tert-butyl ester, monohydrochloride (2.7 g, 13.6 mmol) in 30 mL pyridine. The crude product was purified by chromatography (silica gel: hexane/ethyl acetate). The pure fractions were pooled and concentrated in vacuo to afford 0.5 g of the title compound.

EXAMPLE 30

[S-(R*,R*)]-2-[2-[2-(1-tert-Butoxycarbonyl-3-methylbutylcarbamoyl)-5-methoxy-phenyldisulfanyl]-4-methoxybenzoylamino]-4-methyl-pentanoic acid tert-butyl ester This compound was prepared according to the procedure described in Example 26 using 2,2'-dithiobis[4-methoxybenzoyl chloride] (1.1 g, 2.7 mmol) in 10 mL dichloromethane and L-leucine tert-butyl ester, monohydrochloride (1.5 g, 6.8 mmol) and N-methyl morpholine (1.6 mL, 14.0 mmol) in 25 mL dichloromethane. The crude product was recrystallized from ethyl acetate to yield 1.2 g of the title compound.

EXAMPLE 31

[S-(R*,R*)]-2-[2-[2-(1-tert-Butoxycarbonyl-3-methylbutylcarbamoyl)-4-methoxy-phenyldisulfanyl]-5-methoxybenzoylamino]-4-methyl-pentanoic acid tert-butyl ester This compound was prepared according to the procedure described in Example 26 using 2,2'-dithio-bis[5-methoxybenzoyl chloride] (3.2 g, 8.1 mmol) in 30 mL dichloromethane and L-leucine tert-butyl ester, monohydrochloride (4.2 g, 18.8 mmol) and N-methyl morpholine (4.5 mL, 40.0 mmol) in 30 mL dichloromethane. The crude product was recrystallized from ethyl acetate to yield 2.4 g of the title compound.

EXAMPLE 32

[S-(R*,R*)]-2-[2-[2-(1-tert-Butoxycarbonyl-3-methylbutylcarbamoyl)-6-methyl--phenyldisulfanyl]-3-methylbenzoylamino]-4-methyl-pentanoic acid tert-butyl ester This compound was prepared according to the procedure described in Example 26 using 2,2'-dithiobis[3-methylbenzoyl chloride] (0.8 g, 2.3 mmol) in 10 mL dichloromethane and L-leucine tert-butyl ester, monohydrochloride (1.2 g, 5.8 mmol) in 15 mL pyridine. The crude product was purified by column chromatography (silica gel: hexane/ethyl acetate). The pure fractions were pooled and concentrated in vacuo to afford 0.9 g of the title compound.

EXAMPLE 33

[S-(R*,R*)]-2-[2-[2-(1-tert-Butoxycarbonyl-3-methylbutylcarbamoyl)-5-methyl-phenyldisulfanyl]-4-methylbenzoylamino]-4-methyl-pentanoic acid tert-butyl ester This compound was prepared according to the procedure described in Example 26 using 2,2'dithiobis[4-methylbenzoyl chloride] (1.8 g, 7.8 mmol) in 20 mL dichloromethane, L-leucine, tert-butyl ester, monohydrochloride (4.0, 17.9 mmol), and N-methyl morpholine (4.6 mL, 41.0 mmol) in 60 mL dichloromethane. The crude product was recrystallized from ethyl acetate to yield 1.9 g of the title compound.

EXAMPLE 34

[S-(R*,R*)]-2-[2-[2-(1-tert-Butoxycarbonyl-3-methylbutylcarbamoyl)-3-methyl-phenyldisulfanyl]-6-methylbenzoylamino]-4-methyl-pentanoic acid tert-butyl ester This compound was prepared according to the procedure described in Example 26 using 2,2'dithiobis[6-methylbenzoyl chloride] (1.8 g, 7.8 mmol) in 20 mL dichloromethane, L-leucine,tert-butyl ester, monohydrochloride (4.0, 17.9 mmol), and N-methyl morpholine (4.6 mL, 41 mmol) in 60 mL dichloromethane. The crude product was recrystallized from ethyl acetate to yield 1.9 g of the title compound.

EXAMPLE 35

[S-(R*,R*)]-{2-[2-(1,2-Bis-tert-butoxycarbonyl-ethylcarbamoyl)-phenyldisulfanyl]-benzoylamino}-succinic acid di-tert-butyl ester This compound was prepared according to the procedure described in Example 26 using 2,2'-dithiobis[benzoyl chloride] (1.1 g, 3.2 nmol) in 15 mL dichloromethane and L-aspartic acid di-tert-butyl ester, monohydrochloride (2.0 g, 7.1 nmol) and N-methyl morpholine (1.6 mL, 14.5 mmol) in 30 mL dichloromethane. The crude product was recrystallized from ethyl acetate to yield 1.1 g of the title compound.

EXAMPLE 36

[S-(R*,R*)]-2-{2-[2-(1,3-Bis-tert-butoxycarbonyl-propyl carbamoyl)-phenyldisulfanyl]-benzoylamino}-pentanedioic acid di-tert-butyl ester This compound was prepared according to the procedure described in Example 26 using 2,2'-dithiobis[benzoyl chloride] (1.1 g, 3.2 mmol) in 15 mL dichloromethane and L-glutamic acid di-tert-butyl ester, monohydrochloride (2.0 g, 6.7 mmol) and N-methyl morpholine (1.5 mL, 13.6 mmol) in 30 mL dichloromethane. The crude product was recrystallized from ethyl acetate to yield 0.8 g of the title compound.

EXAMPLE 37

[S-(R*,R*)]-2-{2-[2-(1,4-Bis-tert-butoxycarbonyl-butylcarbamoyl)-phenyldisulfanyl]-benzoylamino}-hexanedioic acid di-tert-butyl ester This compound was prepared according to the procedure described in Example 26 using 2,2'-dithiobis[benzoyl chloride] (1.1 g, 3.2 mmol) in 15 mL dichloromethane and L-2-aminoadipic acid di-tert-butyl ester, monohydrochloride (2.0 g, 7.3 mmol) and N-methyl morpholine (1.7 mL, 15.4 mmol) in 40 mL dichloromethane. The crude product was purified by column chromatography (silica gel:hexane/ethyl acetate/dichloromethane). The pure fractions were pooled and concentrated in vacuo to afford 1.1 g of the title compound.

EXAMPLE 38

[R-(R*,R*)](2-{2-[(tert-Butoxycarbonyl-phenyl-methyl)carbamoyl]-phenyldisulfanyl}-benzoylamino)phenyl-acetic acid tert-butyl ester This compound was prepared according to the procedure described in Example 26 using 2,2'-dithio-bis[benzoyl chloride] (0.4 g, 1.3 mmol) in 10 mL dichloromethane and L-phenylglycine-tert-butyl ester (0.6 g, 2.9 mmol) and triethylamine (0.4 mL, 3.1 mmol) in 30 mL dichloromethane. The crude product was purified by column chromatography (silica gel:hexane/ethyl acetate). The pure fractions were pooled and concentrated in vacuo to afford 0.2 g of the title compound.

EXAMPLE 39

N,N'-[Dithiobis(2,1-phenylenecarbonyl)]bis L-serine bis[O-(1,1-dimethylethyl) bis (1,1'-dimethylethyl) ester This compound was prepared according to the procedure described in Example 26 using 2,2'-dithio-bis[benzoyl chloride] (1.5 g, 4.4 mmol) in 20 mL dichloromethane and L-serine-O-tert-butyl ether-tertbutyl ester, monohydrochloride (2.5 g, 9.8 mmol) and N-methyl morpholine (2.2 mL, 20.2 mmol) in 30 mL dichloromethane. The crude product was recrystallized from ethyl acetate to yield 1.5 g of the title compound.

EXAMPLE 40

N,N-[Dithiobis[2,1-phenylenecarbonylimino]-4,1-phenylen e-sulfonyl] bis L-alanine bis 1,1-dimethylethyl ester This compound was prepared according to the procedure described in Example 26 using 2,2'-dithiobis[benzoyl chloride] (0.9 g, 2.6 mmol) in 10 mL dichloromethane and L-2-(4-amino-benzenesulfonylamino)-propionic acid 1,1'-dimethylethyl ester, (M. N. Divanyan, et al., Khim. Farm., 1982;16:769 (1.5 g, 5.0 mmol) and triethylamine (0.8 mL, 5.5 mmol) in 30 mL dichloromethane. The crude product was purified by column chromatography (silica gel: hexane/ ethyl acetate). The pure fractions were pooled and concentrated in vacuo to afford 0.4 g of the title compound.

EXAMPLE 41

N,N-[Dithiobis[2,1-phenylenecarbonylimino]-4,1-phenylene-carbonylimino] bis L-Alanine bis 1,1-dimethylethyl ester This compound was prepared according to the procedure described in Example 26 using 2,2'-dithiobis[benzoyl chloride] (1.0 g, 2.6 mmol) in 12 mL dichloromethane and L-2-(4-amino-benzoylamino)-propionic acid 1,1'-dimethylethyl ester, (P. A. Reddy, et al., Org. Prep. Proc. Int., 1990;22:117 (2.0 g, 7.3 mmol) and N-methyl morpholine (0.7 mL, 6.0 mmol) in 25 mL dichloromethane. The product precipitated from the reaction mixture and was recovered by filtration to afford 0.8 g of the title compound.

EXAMPLE 42

L,L-2-[(2-{2-[(1-tert-Butoxycarbonyl-3-methyl-butyl)-methyl-carbamoyl]-phenyldisulfanyl}-benzoyl)-methylamino]-4-methyl-pentanoic acid tert-butyl ester This compound was prepared according to the procedure described in Example 26 using 2,2'-dithiobis[benzoyl chloride] (1.2 g, 3.3 mmol) in 10 mL dichloromethane and L-N-methyl-leucine-tert-butyl ester (1.5 g, 7.5 mmol) and triethylamine (1.2 mL, 8.2 mmol) in 30 mL dichloromethane. The crude product was purified by column chromatography (silica gel:hexane/ethyl acetate). The pure fractions were pooled and concentrated in vacuo to afford 1.1 g of the title compound.

EXAMPLE 43

4,4'-[Dithiobis(2,1-phenylenecarbonylimino)]bis butanoic acid bis (1,1-dimethylethyl) ester This compound was prepared according to the procedure described in Example 26 using 2,2'-dithiobis[benzoyl chloride] (2.0 g, 5.7 mmol) in 25 mL dichloromethane and 4-aminobutyric acid-1,1-dimethylethyl ester (J. Xie, et al.,J. Med. Chem., 1989;32:1497 (0.6 g, 2.9 mmol) and N-methylmorpholine (1.3 mL, 11.4 mmol) in 60 mL dichloromethane. The crude product was purified by column chromatography (silica gel:hexane/tetrahyrofuran). The pure fractions were pooled and concentrated in vacuo to afford 0.5 g of the title compound.

EXAMPLE 44

[S-(R*,R*)] 2-{5-Acetylamino-2-[4-acetylamino-2-(1-tert-butoxycarbonyl-3-methyl-butylcarbamoyl)-phenyldisulfanyl]-benzoylamino}-4-methyl-pentanoic acid tertbutyl ester (General method)

A solution of 2,2'-dithiobis(5-acetylaminobenzoic acid) (0.3 g, 0.5 mmol) in 4 mL dimethylformamide was treated with a solution 1,3-dicyclohexylcarbodiimide (0.3 g, 1.2 mmol) and 1-hydroxybenzotriazole hydrate (0.2 g, 1.2 mmol) in 30 mL dichloromethane and allowed to stir for 1.5 hours. The mixture was then treated with L-leucine tert-butyl ester, monohydrochloride (0.4 g, 1.7 mmol) and allowed to stir for 18 hours at ambient temperature. The solvents were removed in vacuo and the residue was dissolved in ethyl acetate and filtered. The ethyl acetate solution was extracted with 0.5N HCl, 8.0% NaHCO$_3$, water, and dried with MgSO$_4$. The filtrate was concentrated in vacuo and the crude solid was recrystallized from dichloromethane to afford 0.2 g of the title compound.

EXAMPLE 45

[S-(R*,R*)] 2-{5-Ethylamino-2-[4-ethylamino-2-(1-tertbutoxycarbonyl-2-methyl-butylcarbamoyl)-phenyldisulfanyl]-benzoylamino}-3-methyl-pentanoic acid tert-butyl ester This compound was prepared according to the procedure described in Example 44 using 2,2'-dithiobis[5-N-ethylaminobenzoic acid] (0.8 g, 2.0 mmol) in 3 mL dimethylforamide, 1,3-dicyclohexylcarbodiimide (0.9 g, 0.43 mmol) and 1-hydroxybenzotriazole hydrate (0.7 g, 4.3 mmol) in 50 mL dichloromethane, and L-isoleucine tert-butyl ester, monohydrochloride (1.1 g, 5.0 mmol). The crude product was purified by column chromatography (silica gel:hexane/ethyl acetate). The pure fractions were pooled and concentrated in vacuo to afford 0.8 g of the title compound.

EXAMPLE 46

[R-(R*,R*)] 2,2'-Dithiobis[N-(2-hydroxy-1-phenylethyl)-benzamide (General method)

A slurry of (R)-2-amino-2-phenylethanol (1.0 g, 7.4 mmol) in 50 mL dichloromethane was allowed to stir with N-methyl-N-(trimethylsilyl)acetamide (3.4 mL, 21.1 mmol) until a homogenous solution occured. The solution was cooled to 0° C. to 5° C. and a solution of 2,2'-dithiobis [benzoyl chloride] (1.0 g, 2.9 mmol) in 20 mL dichloromethane was added. The solution was stirred for 2 hours and 1 mL of 50% aqueous acetic was added causing the crude product to precipitate from solution. This solid was collected by filtration, washed with 1N HCl, water, and recrystallized from dimethylformamide/water to afford 1.2 g of the title compound, mp 235–236° C.

EXAMPLE 47

[S-(R*,R*)] 2,2'-Dithiobis[N-[1-(hydroxymethyl)-3-methylbutyl]-benzamide]

This compound was prepared according to the general procedure described in Example 46 using (R)-2-amino-4-methyl-1-pentanol (1.2 g, 10.7 mmol), N-methyl-N-(trimethylsilyl)acetamide (3.2 mL, 8.6 mmol), 50 mL dichloromethane, and 2,2'-dithiobis[benzoyl chloride] (1.5 g, 4.3 mmol) in 20 mL dichloromethane. The crude product was recrystallized from dimethylformamide/water to afford 0.6 g of the title compound, mp 195–196° C.

EXAMPLE 48

L,L-2-{2-[2-(1-Carboxy-2,2-dimethyl-propylcarbamoyl)-phenyldisulfanyl]-benzoylamino}-3,3-dimethyl-butyric acid This compound was prepared according to the general procedure described in Example 46 using 2-amino-3,3-dimethyl-butyric acid (1.5 g, 11.0 mmol), N-methyl-N-(trimethylsilyl)acetamide (11.1 mL, 69 mmol), 100 mL dichloromethane, and 2,2'-dithiobis[benzoyl chloride] (1.6 g, 4.5 mmol) in 20 mL dichloromethane. The crude product was purified by column chromatography (silica gel: dichloromethane/ethanol). The pure fractions were pooled and concentrated in vacuo to afford 24.0 mg of the title compound, mp 132–135° C.

EXAMPLE 49

2-[2-(2-{2-[1-(1-Carboxy-ethylcarbamoyl]-3-methyl-butylcarbamoyl]-phenyldisulfanyl}-benzoylamino)-4-methylpentanoylamino]-propionic acid, alternatively named (N-[2-[[2-[[1-[[(1-carboxyethyl)aminolcarbonyl]-3-methylbutyl]amino] carbonyl]phenyl] dithiolbenzoyl]) L-Leu-L-Ala This compound was prepared according to the general procedure described in Example 46 using L-leucyl-L-alanine hydrate (1.0 g, 4.9 mmol), N-methyl-N-(trimethylsilyl)acetamide (3.4 mL, 21 mmol), 50 mL dichloromethane, and 2,2'-dithiobis[benzoyl chloride] (0.5 g, 2.0 mmol) in 20 mL dichloromethane. The crude product was recrystallized from dimethylformamide/ethanol/water to afford 0.5 g of the title compound, mp 234–235° C.

EXAMPLE 50

[S-(R*,R*)]-2-{2-[2-(1-Carboxy-2-methyl-butylcarbamoyl)-6-fluoro-phenyldisulfanyl]-3-fluoro-benzoylamino}-3-methyl-pentanoic acid (General method)

To a solution of [S-(R*,R*)]-2-[2-[2-(1-tert-butoxycarbonyl-2-methyl-butylcarbamoyl)-6-fluorophenyldisulfanyl]-3-fluoro- benzoylamino]-3-methylpentanoic acid tert butyl ester (0.6 g ,0.8 mmol) and anisole (1 ml) in 10 mL dichloromethane at 0° C., was added dropwise 10 mL trifluoroacetic acid. The mixture was allowed to warm to ambient temperature. After 4 hours, 5 mL toluene was added and the solvents were removed in vacuo. The crude product was recrystallized from methanol/water to yield 0.2 g of the title compound, mp 188–190° C.

EXAMPLE 51

[s-(R*,R*)]2-{2-[2-(1-carboxy-3-methyl-butylcarbamoyl)-5-fluoro-phenyldisulfanyl]-4-fluoro-benzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-5-fluoro-phenyldisulfanyl]-4-fluorobenzoylamino]-4-methyl-pentanoic acid tert-butyl ester (3.1 g, 4.5 mmol) from Example 27, 30 mL dichloromethane, 30 mL trifluoroacetic acid, and 3.0 mL anisole. The crude product was recrystallized from dimethylformamide/methanol/water to afford 1.6 g of the title compound, mp 261–262° C.

EXAMPLE 52

[S-(R*,R*)] 2-{2-[2-(1-Carboxy-3-methyl-butylcarbamoyl)-4-fluoro-phenyldisulfanyl]-5-fluorobenzoylamino}-4-methyl-pentanoic acid This compound was prepared according to the procedure described in Example 50 using [S-(R R*)-2-[2-[2-(1-tert-butoxycarbonyl-3-methyl-butylcarbamoyl)-4-fluoro-phenyldisulfanyl]-5-fluorobenzoylamino]-4-methyl-pentanoic acid tert-butyl ester (2.1 g, 3.0 mmol) from Example 28, 25 mL dichloromethane, 25 mL trifluoroacetic acid, and 2.5 mL anisole. The crude product was recrystallized from methanol/water to afford 0.3 g of the title compound, mp 246–247° C.

EXAMPLE 53

[S-(R*,R*)] 2{2-[2-(1-carboxy-3-methylbuthylcarbamoyl)-6-methoxy-phenyldisulfanyl]-3-methoxy-benzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-6-methoxy-phenyldisulfanyl]-3-methoxy-benzoylamino]-4-methyl-pentanoic acid tert butyl ester (0.6 g, 0.7 mmol) from Example 29, 10 mL dichloromethane, and 10 mL trifluoroacetic acid. The crude product was dissolved in 20 mL water containing NaHCO$_3$ (90.0 mg, 1.1 mmol), extracted with ethyl acetate, and dilute HCl was added to a pH=2. The product was extracted into ethyl acetate, washed with water, dried with MgSO$_4$, filtered, and the solvent was removed in vacuo to afford 0.3 g of the title compound, mp 131–132° C.

EXAMPLE 54

[S-(R*,R*)] 2-{2-[2-(1-Carboxy-3-methyl-butylcarbamoyl)-5-methoxy-phenyldisulfanyl]-4-methoxybenzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-5-methoxy-phenyldisulfanyl]-4-methoxy-benzoylamino]-4-methyl-pentanoic acid tert-butyl ester (1.2 g, 17.0 mmol) from Example 30, 10 mL dichloromethane, 10 mL trifluoroacetic acid, and 1 mL anisole. The crude product was recrystallized from methanol/water to afford 0.8 g of the title compound, mp 230–231° C.

EXAMPLE 55

[s-(R*,R*)] 2-{2-[2-(1-Carboxy-3-methylbutylcarbamoyl)-4-methoxy-phenyldisulfanyl]-5-methoxy-benzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-4-methoxy-phenyldisulfanyl]-5-methoxybenzoylamino]-4-methyl-pentanoic acid tert-butyl ester (2.4 g, 3.4 mmol) from Example 31, 25 mL dichloromethane, 25 mL trifluoroacetic acid and 2.5 mL anisole. The crude product was recrystallized from methanol/water to afford 0.7 g of the title compound, mp 168–169° C.

EXAMPLE 56

[S-(R*,R*)]2-{2-[2-(1-Carboxy-3-methyl-butylcarbamoyl)-6-methyl-phenyldisulfanyl]-3-methyl-benzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-6-methyl-phenyldisulfanyl]-3-methylbenzoylamino]-4-methyl-pentanoic acid tert-butyl ester (0.9 g, 1.3 mmol) from Example 32, 10 mL dichloromethane, and 10 mL trifluoroacetic acid. The crude product was recrystallized from dimethylformamide/water to afford 0.4 g of the title compound, mp 210–211° C.

EXAMPLE 57

[S-(R*,R*)] 2-{2-[2-(1-Carboxy-3-methylbutylcarbamoyl)-5-methyl-phenyldisulfanyl]-4-methylbenzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-5-methyl-phenyldisulfanyl]-4-methylbenzoylamino]-4-methyl-pentanoic acid tert-butyl ester (1.9 g, 2.8 mmol) from Example 33, 20 mL dichloromethane, 20 mL trifluoroacetic acid and 2.0 mL anisole. The crude product was recrystallized from methanol/water to afford 1.4 g of the title compound, mp 216–218° C.

EXAMPLE 58

L,L-2-{2-[2-(1-Carboxy-3-methyl-butylcarbamoyl)-3-methyl-phenyldisulfanyl]-6-methyl-benzoylamino}-4-methyl-pentanoic acid This compound was prepared according to the procedure described in Example 50 using [S-(R*,R*)]-2-[2-[2-(1-tert-butoxycarbonyl-3-methyl-butylcarbamoyl)-3-methyl-phenyldisulfanyl]-6-methylbenzoylamino]-4-methyl-pentanoic acid tert-butyl ester (1.3 g, 1.9 mmol) from Example 34, 10 mL dichloromethane, and 10 mL trifluoroacetic acid. The crude product was recrystallized from ethanol/water to afford 0.6 g of the title compound, mp 233–235° C.

EXAMPLE 59

L,L-2-[(2-{2-[(1-Carboxy-3-methyl-butyl)-methylcarbamoyl]-phenyldisulfanyl}-benzoyl)-methyl-amino]-4-methyl-pentanoic acid This compound was prepared according to the procedure described in Example 50 using L,L-2-[(2-{2-[(1-tert-butoxycarbonyl-3-methyl-butyl)-methylcarbamoyl]-phenyldisulfanyl}-benzoyl)-methyl-amino]-4-methyl-pentanoic acid tert-butyl ester (1.1 g, 1.7 mmol) from Example 42, 10 mL dichloromethane, and 10 mL trifluoroacetic acid. The crude product was recrystallized from methanol/water to afford 0.4 g of the title compound, mp 120° C.

EXAMPLE 60

[S-(R*,R*)] 2-{5-Acetylamino-2-[4-acetylamino-2-(1-carboxy-3-methyl-butylcarbamoyl)-phenyldisulfanyl]-benzoylamino}-4-methyl-pentanoic acid This compound was prepared according to the procedure described in Example 50 using [S-(R*,R*)] 2-{5-acetylamino-2-[4-acetylamino-2-(1-tert-butoxycarbonyl-3-methyl-butylcarbamoyl)-phenyldisulfanyl]-benzoylamino}-4-methyl-pentanoic acid tert-butyl ester (0.2 g, 0.2 mmol) from Example 44, 10 mL dichloromethane, and 10 mL trifluoroacetic acid. The crude product was recrystallized from dimethylformamide/water to afford 0.1 g of the title compound, mp 241–242° C.

EXAMPLE 61

N,N'-[Dithiobis[[5-(ethylamino)-2,1-phenylene]carbonyl]] bis L-iso-leucine

This compound was prepared according to the procedure described in Example 50 using [S-(R*,R*)] 2-{5-ethylamino-2-[4-ethylamino-2-(1-tert-butoxycarbonyl-2-methyl-butylcarbamoyl)-phenyldisulfanyl]-benzoylamino}-3-methyl-pentanoic acid tert-butyl ester (0.8 g, 1.1 mmol) from Example 45, 10 mL dichloromethane, and 10 mL trifluoroacetic acid. The product was washed with hexane/ether to afford 0.6 of the title compound, mp 97–100° C.

EXAMPLE 62

L,L-2-{2-[2-(1,2-Dicarboxy-ethylcarbamoyl)-phenyldisulfanyl]-benzoylamino}-succinic acid This compound was prepared according to the procedure described in Example 50 using [S-(R*,R*)]-{2-[2-(1,2-bistert-butoxycarbonyl-ethylcarbamoyl)-phenyldisulfanyl]-benzoylamino}-succinic acid di-tert-butyl ester (1.1 g, 1.4 mmol) from Example 35, 10 mL dichloromethane, 10 mL trifluoroacetic acid, and 1.0 mL anisole. The crude product was recrystallized from acetone/ethyl acetate to afford 0.4 g of the title compound, mp 177–178° C.

EXAMPLE 63

L,L-2-{2-[2-(1,3-Dicarboxy-propylcarbamoyl)-phenyldisulfanyl]-benzoylamino}-pentanedioic acid This compound was prepared according to the procedure described in Example 50 using [S-(R*,R*)]-2-{2-[2-(1,3-bis-tert-butoxycarbonyl-propylcarbamoyl)-phenyldisulfanyl]-benzoylamino}-pentanedioic acid di-tert-butyl ester (0.8 g, 1.0 mmol) from Example 36, 10 mL dichloromethane, 10 mL trifluoroacetic acid, and 1.0 mL anisole. The crude product was dissolved in 20 mL water containing NaHCO$_3$, extracted with ethyl acetate, and dilute HCl was added to a pH=2. The resulting solid was recovered by filtration to afford 0.3 g of the title compound, mp 205–206° C.

EXAMPLE 64

[S-(R*,R*)] 2-{2-[2-(1,4-Dicarboxy-butylcarbamoyl)-phenyldisulfanyl]-benzoylamino}-hexanedioic acid This compound was prepared according to the procedure described in Example 50 using [S-(R*,R*)]-2-{2-[2-(1,4-bis-tert-butoxycarbonyl-butylcarbamoyl)-phenyldisulfanyl]-benzoylamino}-hexanedioic acid di-tert-butyl ester (1.1 g, 1.4 mmol) from Example 37, 10 mL dichloromethane, 10 mL trifluoroacetic acid, and 1 mL anisole. The crude product was recrystallized from methanol/dimethylformamide/water to afford 0.6 g of the title compound, mp 259–260° C.

EXAMPLE 65

4,4'-[Dithiobis(2,1-phenylene carbonylimino)]bis butanoic acid

This compound was prepared according to the procedure described in Example 50 using 4,4'-[dithiobis(2,1-phenylenecarbonylimino)]bis butanoic acid bis (1,1-dimethylethyl) ester (0.5 g, 0.9 mmol) from Example 43, 10 mL dichloromethane, 10 mL trifluoroacetic acid, and 1 mL anisole. The crude product was recrystallized from methanol/dimethylformamide/water to afford 0.6 g of the title compound, mp 165–166° C.

EXAMPLE 66

L-L-2-[4-(2-{2-[4-(1-Carboxy-ethylsulfamoyl)-phenylcarbamoyl]-phenyldisulfanyl}-benzoylamino)-benzenesulfonylamino]-propionic acid This compound was prepared according to the procedure described in Example 50 using N,N-[dithiobis[2,1-phenylenecarbonylimino]-4,1-phenylene-sulfonyl] bis L-alanine bis 1,1-dimethylethyl ester (0.4 g, 0.4 mmol) from Example 40, 10 mL dichloromethane, and 10 mL trifluoroacetic acid. The crude product was recrystallized from ethanol/water to afford 0.2 g of the title compound, mp 227–229° C.

EXAMPLE 67

[S-(R*,R*)]2-[4-(2-{2-[4-(1-Carboxy-ethylcarbamoyl)-phenylcarbamoyl]-phenyldisulfanyl}-benzoylamino)-benzoylamino]-propionic acid This compound was prepared according to the procedure described in Example 50 using N,N-[dithiobis[2,1-phenylenecarbonylimino]-4,1-phenylenecarbonylimino] bis L-alanine bis 1,1-dimethylethyl ester (0.8 g, 1.0 mmol) from Example 41, 10 mL dichloromethane, 10 mL trifluoroacetic acid, and 1 mL anisole. The crude product was recrystallized from dimethylformamide/water to afford 0.3 g of the title compound, mp 265° C.

EXAMPLE 68

[R-(R*,R*)] (2-{2-[(Carboxy-phenyl-methyl)-carbamoyl]-phenyldisulfanyl}-benzoylamino)-phenyl-acetic acid This compound was prepared according to the procedure described in Example 50 using [R-(R*,R*)] (2-{2-[(tert-butoxycarbonyl-phenyl-methyl)-carbamoyl]-phenyldisulfanyl}-benzoylamino)-phenyl-acetic acid tert-butyl ester (0.2 g, 0.3 mmol) from Example 38, 10 mL dichloromethane, and 10 mL trifluoroacetic acid. The crude product was stirred with ether/hexane and filtered to afford 73.0 mg of the title compound, mp 231–232° C.

EXAMPLE 69

[S-(R*,R*)] 3-tert-Butoxy-2-{2-[2-(2-tert-butoxy-1-carboxy-ethylcarbamoyl)-phenyldisulfanyl]-benzoylamino}-propionic acid A solution of N,N'-[dithiobis(2,1-phenylene carbonyl)]bis L-serine bis[O(1,1-dimethylethyl) bis (1,1-dimethylethyl) ester (1.0 g, 1.4 mmol) from Example 39, in 30 mL methanol was treated with 8 mL of 1N NaOH and allowed to stir for 18 hours. The methanol was removed in vacuo and the residual was diluted with water and extracted with ethyl acetate. A slow stream of oxygen was passed thru the aqueous layer while dilute HCl was added to maintain a pH=6–7. After the disulfide formation was complete (2–18 hours), dilute HCL was added to a pH=3. The product was collected by filtration, washed with water, dried and was recrystallized from ethyl acetate to afford 0.4 g of the title compound, mp 206–207° C.

EXAMPLE 70

2,2'-Dithiobis[5-methoxy-benzamide] (General method)

A saturated solution of ammonia in pyridine (15 mL) at 0° C. to 5° C. was treated with a solution of 2,2'-dithiobis[5-methylbenzoyl chloride] (0.3 g, 0.6 mmol) in 8 mL dichloromethane. The solution was allowed to stir for 4 hours, the solvents were removed under reduced pressure, and the residue was triturated with dilute HCl. The crude product was recrystallized from dimethylformamide and dilute NaHCO$_3$ to afford 91 mg of the title compound, mp 188–189° C.

EXAMPLE 71

2,2'-Dithiobis[3-methoxy-benzamide]

This compound was prepared according to the procedure described in Example 70 using 2,2'-dithiobis[3-methoxybenzoyl chloride] (0.9 g, 2.3 mmol) in 10 mL dichloromethane and 15 mL of pyridine saturated with ammonia. The crude product was purified by column chromatography (silica gel:dichloromethane/acetonitrile). The pure fractions were pooled and concentrated in vacuo to afford 92.0 mg of the title compound, mp 188–189° C.

EXAMPLE 72

2,2'-Dithiobis[3-methyl-benzamide]

This compound was prepared according to the procedure described in Example 70 using 2,2'-dithiobis[3- methylbenzoyl chloride] (0.9 g, 2.3 mmol) in 10 mL dichloromethane and 30 mL of pyridine saturated with ammonia. The crude product was purified by column chromatography (silica gel: dichloromethane/tetrahydrofuran). The pure fractions were pooled and concentrated in vacuo to afford 72.0 mg of the title compound, mp 189–190° C.

EXAMPLE 73

2,2'-Dithiobis[5-[(2,2-dimethyl-1-oxopropyl)amino]-benzamide] (General method)

2,2'-Dithiobis-5-aminobenzamide (0.7 g, 2.1 mmol) was dissolved in 36 mL of pivalic acid at reflux and was reacted with pivalic anhydride (1.1 mL, 5.3 mmol). The solution was refluxed for an additional hour, cooled to 40° C., and ether was added. The crude product was collected by filtration and recrystallized from dimethylformamide/water to afford 0.4 g of the title compound, mp 288–289° C.

EXAMPLE 74

2,2'-Dithiobis[5-[(trifluoroacetyl)amino]-benzamide

This compound was prepared according to the procedure described in Example 73 using 2,2'-dithiobis-5-aminobenzamide (0.7 g, 2.1 mmol), trifluoroacetic acid (4 mL), and trifluoroacetic anhydride (0.7 mL, 5.2 mmol). The crude compound was recrystallized from dimethylformamide/water to afford 0.1 g of the title compound, mp 262–263° C.

EXAMPLE 75

2,2'-Dithiobis[5-(benzoylamino)-benzamide]

A solution of 2,2'-dithiobis-5-aminobenzamide (0.5 g, 1.5 mmol) in 30 mL dimethylformamide and 20 mL tetrahydrofuran at 0° C. to 5° C., was reacted with benzoyl chloride (0.4 g, 3.3 mmol) and the solution was allowed to stir for 3 hours. Water was added to the reaction, the product was isolated by filtration, and recrystallized from dimethylformamide/tetrahydrofuran/water to afford 0.1 g of the title compound, mp 273–274° C.

EXAMPLE 76

3,3'-[Dithiobis(2,1-phenylenecarbonylimino)] bispropionic acid

To a solution of sodium ethoxide (13.7 g, 200.0 mmol) in 100 mL ethanol was added a solution 3-amino-propionic acid (30.0 g, 300.0 mmol) in 100 mL ethanol and the mixture was cooled to 0–5° C. The resulting slurry was reacted with 2,2'-dithiobisbenzoyl chloride (17.2 g, 50.1 mmol) and the reaction was allowed to warm to ambient temperature. The crude product was recovered by filtration, dried, and dissolved in water. The solution was treated with charcoal, filtered, and concentrated. HCl was added to a pH=3. The resulting solid was recovered by filtration and recrystallized from ethanol/water to afford 12.0 g of the title compound, mp 201–203° C.

EXAMPLE 77

2,2'-Dithiobis[N-[4-(1,1-dimethylethyl)phenyl] benzamide] (General method)

A solution of 2,2'-dithiobisbenzoyl chloride (1.20 g, 3.50 mmol) in 25 mL of dichloromethane was added to a solution of 4-tert-butylaniline (1.04 g, 6.99 mmol) in 8 mL of pyridine at 23° C. The reaction mixture was stirred for 18 hours at 23° C. under nitrogen atmosphere. The mixture was concentrated, the residue triturated with 5% aqueous HCl, and the resulting solid was collected by filtration and washed with water to yield the crude product. The crude material was recrystallized from ethyl ether-ethanol to yield 0.24 g of the title compound, mp 135–138° C.

EXAMPLE 78

2,2'-Dithiobis[N-(3-methylphenyl)benzamide]

This compound was prepared according to the general method of Example 77 using 2,2'-dithiobisbenzoyl chloride (2.00 g, 5.83 mmol) in 50 mL of dichloromethane and m-toluidine (1.24 g, 11.6 mmol) in 10 mL of pyridine. The crude product was recrystallized from ethyl ether-ethyl acetate to yield 1.18 g of the title compound, mp 193–195° C.

EXAMPLE 79

2,2'-Dithiobis[N-[4-nitro-3-(trifluoromethyl)phenyl]-benzamide]

This compound was prepared according to the general method of Example 77 using 2,2'-dithiobisbenzoyl chloride (2.00 g, 5.83 mmol) in 50 mL of dichloromethane and 4-nitro-3-(trifluoromethyl)aniline (2.39 g, 11.6 mmol) in 19 mL of pyridine. The crude product was recrystallized from ethyl ether to yield 0.25 g of the title compound, mp 167–169° C.

EXAMPLE 80

2,2'-Dithiobis[N-(3-bromophenyl)benzamide]

This compound was prepared according to the general method of Example 77 using 2,2'-dithiobisbenzoyl chloride (2.00 g, 5.83 mmol) in 50 mL of dichloromethane and 3-bromoaniline (1.98 g, 11.6 mmol) in 16 mL of pyridine. The crude product was recrystallized from ethyl acetate-hexanes to yield 1.99 g of the title compound, mp 194–196° C.

EXAMPLE 81

2,2'-Dithiobis[N-[3,5-bis(trifluoromethyl)phenyl]-benzamide]

This compound was prepared according to the general method of Example 77 using 2,2'-dithiobisbenzoyl chloride (2.00 g, 5.83 mmol) in 50 mL of dichloromethane and 3,5-bis(trifluoromethyl)aniline (2.66 g, 11.6 mmol) in 21 mL of pyridine. The crude product was recrystallized from ethyl acetate-hexanes (1:9) to yield 0.34 g of the title compound, mp 213–214° C.

EXAMPLE 82

2,2'-Dithiobis[N-[4-chloro-3-(trifluoromethyl) phenyl] benzamide]

This compound was prepared according to the general method of Example 77 using 2,2'-dithiobisbenzoyl chloride (2.00 g, 5.83 mmol) in 50 mL of dichloromethane and 2-amino-5-chlorobenzotrifluoride (2.30 g, 11.6 mmol) in 18 mL of pyridine. The crude product was recrystallized from ethyl ether-hexanes to yield 0.59 g of the title compound, mp 129–131° C.

EXAMPLE 83

2,2'-Dithiobis[N-(3,4-dichlorophenyl)benzamide]

This compound was prepared according to the general method of Example 77 using 2,2'-dithiobisbenzoyl chloride (1.04 g, 3.03 mmol) in 25 mL of dichloromethane and 3,4-dichloroaniline (0.982 g, 6.06 mmol) in 8 mL of pyridine. The crude product was recrystallized from ethyl acetate-hexanes to yield 0.184 g of the title compound, mp 230–233° C.

EXAMPLE 84

2,2'-Dithiobis[N-(2,4-dichlorophenyl)benzamide]

This compound was prepared according to the general method of Example 77 using 2,2'-dithiobisbenzoyl chloride (2.00 g, 5.83 mmol) in 50 mL of dichloromethane and 2,4-dichloroaniline (1.89 g, 11.7 mmol) in 15 mL of pyridine. The crude product was triturated with a hot mixture of ethyl acetate, ethanol and methanol (1:1:1) and filtered to yield 0.64 g of the title compound, mp 227–228° C.

EXAMPLE 85

2,2'-Dithiobis[N-(3,4-dimethylphenyl)benzamide]

This compound was prepared according to the general method of Example 77 using 2,2'-dithiobisbenzoyl chloride (1.12 g, 3.26 mmol) in 25 mL of dichloromethane and 3,4-dimethylaniline (0.79 g, 6.52 mmol) in 8 mL of pyridine. The crude product was triturated with ethyl ether and filtered to yield 0.28 g of the title compound, mp 224–227° C.

EXAMPLE 86

2,2'-Dithiobis[N-(3,5-dichlorophenyl)benzamide]

This compound was prepared according to the general method of Example 77 using 2,2'-dithiobisbenzoyl chloride (2.00 g, 5.83 mmol) in 50 mL of dichloromethane and 3,5-dichloroaniline (1.87 g, 11.7 mmol) in 15 mL of pyridine. The crude product was recrystallized from ethanol, then ethyl ether to yield 0.78 g of the title compound, mp 235–236° C.

EXAMPLE 87

2,2'-Dithiobis[N-(4-fluorophenyl)benzamide]

This compound was prepared according to the general method of Example 77 using 2,2'-dithiobisbenzoyl chloride (1.00 g, 2.92 mmol) in 20 mL of dichloromethane and 4-fluoroaniline (0.657 g, 5.91 mmol) in 5 mL of pyridine. The crude product was triturated with hot ethanol-ethyl acetate mixture, filtered, and recrystallized from ethanol-DMF to yield 0.14 g of the title compound, mp 242–244° C.

EXAMPLE 88

2,2'-Dithiobis[N-[3-(trifluoromethyl)phenyl]benzamide]

This compound was prepared according to the general method of Example 77 using 2,2'-dithiobisbenzoyl chloride (2.00 g, 5.83 mmol) in 50 mL of dichloromethane and 3-aminobenzotrifluoride (1.87 g, 11.6 mmol) in 15 mL of pyridine. The crude product was recrystallized from ethanol, then ethyl ether to yield 0.519 g of the title compound, mp 167–168° C.

EXAMPLE 89

2,2'-Dithiobis[N-(2-methoxhenyl)benzamide]

This compound was prepared according to the general method of Example 77 using 2,2'-dithiobisbenzoyl chloride (2.00 g, 5.83 mmol) in 50 mL of dichloromethane and o-anisidine (1.42 g, 11.5 mmol) in 10 mL of pyridine. The crude product was recrystallized from ethanol-ethyl acetate, then again from acetonitrile-DMF to yield 0.634 g of the title compound, mp 154–155° C.

EXAMPLE 90

3,3'-[Dithiobis(2,1-phenylenecarbonylimino)]bis-2-thiophenecarboxylic acid, dimethyl ester (general method)

A solution of 2,2'-dithiobisbenzoyl chloride (2.00 g, 5.83 mmol) in 50 mL of dichloromethane was added to a solution of methyl 3-amino-2-thiophenecarboxylate (1.82 g, 11.6 mmol) in 14 mL of pyridine at 23° C. The reaction mixture was stirred for 18 hours at 23° C. under nitrogen atmosphere. The precipitate formed was collected by filtration, then triturated with 5% aqueous HCl and washed with water to yield the crude product. The crude material was recrystallized first from ethanol, then from acetonitrile-DMF to yield 2.0 g of the title compound, mp 250–252° C.

EXAMPLE 91

2,2'-Dithiobis[N-[4-(trifluoromethyl)phenyl]benzamide]

This compound was prepared according to the general method of Example 77 using 2,2'-dithiobisbenzoyl chloride (1.12 g, 3.26 mmol) in 25 mL of dichloromethane and 4-aminobenzotrifluoride (1.05 g, 6.53 mmol) in 8 mL of pyridine. The crude product was recrystallized from water-DMF to yield 0.47 g of the title compound, mp 272–275° C.

EXAMPLE 92

2,2'-Dithiobis[N-(5-bromo-2-pyrimidinyl)benzamide]

This compound was prepared according to the general method of Example 77 using 2,2'-dithiobisbenzoyl chloride (2.00 g, 5.83 mmol) in 50 mL of dichloromethane and 2-amino-5-bromopyrimidine (2.03 g, 11.7 mmol) in 16 mL of pyridine. The crude product was triturated with a hot mixture of ethyl acetate and ethanol, filtered, and recrystallized first from DMF, then from acetonitrile-DMF to yield 0.40 g of the title compound, mp 249–253° C.

EXAMPLE 93

2,2'-Dithiobis[N-(4-cyanophenyl)benzamide]

This compound was prepared according to the general method of Example 77 using 2,2'-dithiobisbenzoyl chloride (2.00 g, 5.83 mmol) in 50 mL of dichloromethane and 4-aminobenzonitrile (1.38 g, 11.7 mmol) in 11 mL of pyridine. The crude product was triturated with a hot mixture of ethyl acetate and ethanol (1:1), filtered, and recrystallized from ethanol-DMF-water to yield 0.37 g of the title compound, mp 239–241° C.

EXAMPLE 94

2.2'-Dithiobis[N-[4-(methylsulfonyl)phenyl]benzamide]

This compound was prepared according to the general method of Example 77 using 2,2'-dithiobisbenzoyl chloride (2.00 g, 5.83 mmol) in 50 mL of dichloromethane and 4-aminophenyl methyl sulfone (2.00 g, 11.7 mmol) in 16 mL of pyridine. The crude product was recrystallized from acetonitrile-DMF to yield 2.0 g of the title compound, mp 236–238° C.

EXAMPLE 95

2,2'-Dithiobis[N-(6-chloro-4-pyrimidinyl) benzamide]

This compound was prepared according to the general method of Example 90 using 2,2'-dithiobisbenzoyl chloride (2.00 g, 5.83 mmol) in 50 mL of dichloromethane and 4-amino-6-chloropyrimidine (1.51 g, 11.7 mmol) in 12 mL of pyridine. The crude product was triturated with a hot mixture of ethyl acetate and ethanol, filtered, and recrystallized from acetonitrile-DMF to yield 0.38 g of the title compound, mp 254–256° C.

EXAMPLE 96

2,2'-dithiobis[N-(4-iodophenyl)benzamide]

This compound was prepared according to the general method of Example 77 using 2,2'-dithiobisbenzoyl chloride (2.00 g, 5.83 mmol) in 50 mL of dichloromethane and 4-iodoaniline (2.54 g, 11.6 mmol) in 20 mL of pyridine. The crude product was recrystallized from water-DMF to yield 1.48 g of the title compound, mp 268–271° C. (dec.).

EXAMPLE 97

2,2'-Dithiobis[N-(2-methylphenyl)benzamide]

This compound was prepared according to the general method of Example 77 using 2,2'-dithiobisbenzoyl chloride (2.00 g, 5.83 mmol) in 50 mL of dichloromethane and o-toluidine (1.25 g, 11.7 mmol) in 10 mL of pyridine. The crude product was triturated with a hot mixture of ethyl acetate and ethanol and recrystallized from acetonitrile-DMF to yield 0.11 g of the title compound, mp 224–225° C. (dec.).

EXAMPLE 98

2,2'-Dithiobis[N-(2-ethylphenyl)benzamide]

This compound was prepared according to the general method of Example 90 using 2,2'-dithiobisbenzoyl chloride (2.00 g, 5.83 mmol) in 50 mL of dichloromethane and 2-ethylaniline (1.40 g, 11.6 mmol) in 12 mL of pyridine. The crude product was recrystallized from acetonitrile-DMF to yield 1.0 g of the title compound, mp 255–256° C.

EXAMPLE 99

2,2'-Dithiobis[N-4-pyrimidinyl benzamide]

This compound was prepared according to the general method of Example 90 using 2,2'-dithiobisbenzoyl chloride (3.00 g, 8.74 mmol) in 75 mL of dichloromethane and 4-aminopyrimidine (1.66 g, 17.5 mmol) in 14 mL of pyridine. The crude product was triturated with a hot mixture of acetonitrile and DMF, filtered, and recrystallized from water-DMF to yield 0.08 g of the title compound, mp 234–235° C.

EXAMPLE 100

2,2'-Dithiobis[N-(2-chlorophenyl)benzamide]

This compound was prepared according to the general method of Example 90 using 2,2'-dithiobisbenzoyl chloride (2.00 g, 5.83 mmol) in 50 mL of dichloromethane and 4-amino-6-chloropyrimidine (2.39 g, 11.6 mmol) in 19 mL of pyridine. The crude product was recrystallized first from ethanol-acetone, then from acetonitrile-DMF to yield 0.37 g of the title compound, mp 247–249° C.

EXAMPLE 101

2,2'-Dithiobis[N-(3-nitrophenyl)benzamide]

This compound was prepared according to the general method of Example 77 using 2,2'-dithiobisbenzoyl chloride (2.00 g, 5.83 mmol) in 50 mL of dichloromethane and 3-nitroaniline (1.60 g, 11.6 mmol) in 13 mL of pyridine. The crude product was recrystallized once from ethanol-ether, then twice from acetonitrile-DMF-water to yield 0.79 g of the title compound, mp >270° C.

EXAMPLE 102

2,2'-Dithiobis[N-[2-(aminosulfonyl)phenyl] benzamide]

This compound was prepared according to the general method of Example 77 using 2,2'-dithiobisbenzoyl chloride (2.00 g, 5.83 mmol) in 50 mL of dichloromethane and 2-aminobenzenesulfonamide (2.00 g, 11.6 mmol) in 16 mL of pyridine. The reaction mixture was stirred for 6 days at 23° C. under nitrogen atmosphere. The crude product was. recrystallized from acetonitrile to yield 0.70 g of the title compound, mp 150–151° C. (dec.).

EXAMPLE 103

2,2'-Dithiobis[N-[2-(1-methylethyl)phenyl] benzamide]

This compound was prepared according to the general method of Example 90 using 2,2'-dithiobisbenzoyl chloride (2.00 g, 5.83 mmol) in 50 mL of dichloromethane and 2-isopropylaniline (1.60 g, 11.6 mmol) in 13 mL of pyridine. The crude product was recrystallized twice from acetonitrile-DMF to yield 0.45 g of the title compound, mp 235–237° C.

EXAMPLE 104

2,2'-Dithiobis[N-(3-iodophenyl)benzamide]

This compound was prepared according to the general method of Example 77 using 2,2'-dithiobisbenzoyl chloride (3.00 g, 8.74 mmol) in 75 mL of dichloromethane and 3-iodoaniline (3.82 g, 17.5 mmol) in 17 mL of pyridine. The crude product was triturated with hot ethanol, filtered, and recrystallized first from water-DMF, then from ethyl acetate-ether to yield 0.45 g of the title compound,. mp 184–186° C. (dec.).

EXAMPLE 105

[4-(2-{2-[4-(Diethoxy-phosphorylmethyl)-phenylcarbamoyl]-phenyldisulfanyl}-benzoylamino)-benzyl]-phosphonic acid diethyl ester This compound was prepared according to the general method of Example 77 using 2,2'-dithiobisbenzoyl chloride (2.00 g, 5.83 mmol) in 50 mL of dichloromethane and diethyl 4-aminobenzylphosphonate (2.90 g, 11.6 mmol) in 23 mL of pyridine. The reaction mixture was stirred for 3 days at 23° C. under nitrogen atmosphere. The crude product was recrystallized from acetonitrile-DMF to yield 2.60 g of the title compound, mp 237–238° C. (dec.).

EXAMPLE 106

4,4'-[dithiobis(2,1-phenylenecarbonylimino) bisbenzoic acid] (General method)

To a suspension of 4-aminobenzoic acid (1.60 g, 11.6 mmol) in 20 mL of pyridine, was added N-methyl-N-trimethylsilylacetamide (4.25 g, 29.2 mmol), the mixture was stirred until all the solid dissolved, then a solution of 2,2'-dithiobisbenzoyl chloride (2.00 g, 5.83 mmol) in 50 mL of dichloromethane was added. The resulting reaction mixture was stirred for 18 hours at 23° C. under nitrogen atmosphere. The mixture was then concentrated and the residue was triturated with 5% aqueous HCl. The resulting solid was collected by filtration and washed with water to yield the crude product. The crude material was recrystallized twice from acetonitrile-DMF, then triturated with hot acetonitrile and filtered to yield 0.075 g of the title compound, mp >285° C.

EXAMPLE 107

2,2'-dithiobis(2,1-phenylenecarbonylimino) bisbenzoic acid

This compound was prepared according to the general method of Example 106 using a suspension of 2-aminobenzoic acid (2.40 g, 17.5 mmol) in 24 mL of pyridine, N-methyl-N-trimethylsilylacetamide (6.33 g, 43.6 mmol) and 2,2'-dithiobisbenzoyl chloride (3.00 g, 8.74 mmol) in 75 mL of dichloromethane. The reaction mixture was stirred for 4 days at 23° C. under nitrogen atmosphere. The crude material was triturated with acetonitrile. A solid was formed, which was collected by filtration and recrystallized from acetonitrile-DMF-water to yield 0.90 g of the title compound, mp 242–245° C. (dec.).

EXAMPLE 108

(4-{2-[2-(4-Carboxymethyl-phenylcarbamoyl)-phenyldisulfanyl]-benzoylamino}-phenyl)-acetic acid This compound was prepared according to the general method of Example 106 using a suspension of 4-aminophenylacetic acid (1.80 g, 11.6 mmol) in 16 mL of pyridine, N-methyl-N-trimethylsilylacetamide (4.18 g, 28.8 mmol) and 2,2'-dithiobisbenzoyl chloride (2.00 g, 5.83 mmol) in 50 mL of dichloromethane. The reaction mixture was stirred for 2 days at 23° C. under nitrogen atmosphere. The crude material was triturated with acetonitrile, filtered, recrystallized from acetonitrile-DMF-water, triturated with methanol, and filtered to yield 0.47 g of the title compound, mp 257–260° C.

EXAMPLE 109

2,2'-Dithiobis[N-(4-aminophenyl)benzamide] dihydrochloride

To a solution of 2,2'-dithiobis[N-(4-nitrophenyl) benzamide] (0.309 g, 0.565 mmol) in 75 mL of methanol, was added Ra-Ni (0.3 g). The resulting reaction mixture was stirred at 23° C. for 30 hours under hydrogen atmosphere. The catalyst was removed by filtration, and the filtrate was mixed with 10 mL of concentrated aqueous HCl, then concentrated in vacuo. When the total volume was reduced down to 10 mL, a solid formed, which was collected by filtration, triturated with acetonitrile, and filtered to yield 0.124 g of the title compound, mp >260° C.

EXAMPLE 110

2,2'-Dithiobis[N-[4-(aminocarbonyl)phenyl] benzamide]

This compound was prepared according to the general method of Example 77 using 2,2'-dithiobisbenzoyl chloride (4.00 g, 11.7 mmol) in 100 mL of dichloromethane and 4-aminobenzamide (3.20 g, 23.5 mmol) in 26 mL of pyridine. The crude product was triturated with a hot mixture of acetonitrile and DMF, filtered, recrystallized from ethanol-water-DMF, triturated with a hot mixture of methanol and DMF, and filtered to yield 0.563 g of the title compound, mp >270° C.

EXAMPLE 111

2,2'-Dithiobis[N-2-(dimethylamino)ethylbenzamide]

A solution of 2,2'-dithiobisbenzoyl chloride (1.0 g, 3.0 mmol) in 20 mL of dichloromethane was added dropwise to a solution of N,N-dimethylethylenediamine (0.8 mL, 7.0 mmol) and triethylamine (1.2 mL, 9.0 mmol) in 20 mL of dichloromethane at 0° C. The mixture was stirred for 40 hours at room temperature and was then washed with brine, dried over $MgSO_4$ and concentrated to give 0.9 g of an oily solid. The solid was redissolved in chloroform, dried, and concentrated to yield 0.82 g of the title compound as an oil;

NMR ($CDCl_3$): δ 8.02 (d, 2H), 7.56 (m, 4H), 7.39 (t, 4H), 4.06 (t, 4H), 2.74 (t, 4H), 2.40 (s, 12H).

EXAMPLE 112

{2-[2-(Morpholine-4-carbonyl)-phenyldisulfanyl]-phenyl}-morpholin-4-yl-methanone A solution of 2,2'-dithiobisbenzoyl chloride (1.0 g, 3.0 mmol) in 20 mL of dichloromethane was added dropwise to a solution of morpholine (0.64 mL, 7.0 mmol) and triethylamine (1.2 mL, 9.0 mmol) in 20 mL of dichloromethane at 0° C. The mixture was stirred for 16 hours at room temperature and was then washed with 1N HCL, brine, dried over $MgSO_4$ and concentrated to yield 1.12 g of the title compound as a foam, mp 103–110° C.;

NMR ($CDCL_3$): δ 7.68 (m, 2H), 7.32 (m, 6H), 3.79 (bs, 8H), 3.61 (bs, 4H), 3.25 (bs, 4H).

EXAMPLE 113

{2-[2-(Thiomorpholine-4-carbonyl)-phenyldisulfanyl]-phenyl}-thiomorpholin-4-yl-methanone This compound was prepared according to the general method of Example 112 using 2,2'-dithiobisbenzoyl chloride (1.0 g, 3.0 mmol) in 20 mL of dichloromethane and thiomorpholine (0.75 mL, 7.0 mmol), triethylamine (1.2 mL, 9.0 mmol) in 20 mL of dichloromethane, to give 1.08 g of the title compound as a foam, mp 90–92° C.;

NMR ($CDCL_3$): δ 7.70 (dd, 2H), 7.36 (m, 2H), 7.28 (m, 2H), 7.19 (m, 2H), 4.06 (bs, 4H), 3.52 (bs, 4H), 2.76 (bs, 4H), 2.55 (bs, 4H).

EXAMPLE 114

4,4'-[Dithiobis(2,1-phenylenecarbonyl)]bis-,bis(1,1-dimethylethyl) ester-1-piperazinecarboxylic acid This compound was prepared according to the general method of Example 112 using 2,2'-dithiobisbenzoyl chloride (1.0 g, 3.0 mmol) in 20 mL of dichloromethane and t-butyl piperazinecarboxylate (1.4 g, 7.5 mnmol), triethylamine (1.2 mL, 9.0 mmol) in 20 mL of dichloromethane. The crude product was chromatographed (SiO$_2$, CHCl$_3$/MEOH 97/3) to give 1.01 g of the title compound as a solid, mp 96–99° C.;

NMR (CDCL$_3$): δ 7.68 (d, 2H), 7.32 (m, 4H), 7.20 (m, 2H), 3.78 (bs, 4H), 3.54 (bs, 4H), 3.38 (bs, 4H), 3.23 (bs, 4H), 1.48 (s, 18H).

EXAMPLE 115

2,2'-Dithiobis(N-cyclopropylbenzamide)

A solution of 2,2'-dithiobisbenzoyl chloride (1.0 g, 3.0 mmol) in 20 mL of dichloromethane was added dropwise to a solution of cyclopropylamine (0.52 mL, 7.5 mmol) and triethylamine (1.2 mL, 9.0 mmol) in 20 mL of dichloromethane. A solid formed immediately, the mixture was stirred for 3 hours and then filtered. The solid was dried to yield 0.65 g of the title compound, mp 257–259° C.;

NMR (DMSO-d$_6$): δ 8.62 (d, 2H), 7.61 (t, 4H), 7.44 (t, 2H), 7.29 (t, 2H), 2.87 (m, 2H), 0.73 (m, 4H), 0.61 (m, 4H).

EXAMPLE 116

{2-[2-(Piperazine-1-carbonyl)-phenyldisulfanyl]-phenyl}-piperazine-1-ylmethanone HCl salt A solution of 4,4'-[dithiobis(2,1-phenylenecarbonyl)]bis-, bis(1,1-dimethylethyl) ester-1-piperazinecarboxylic acid, (0.61 g, 0.95 mmol) from Example 114 in 30 mL of dichloromethane was cooled to 0° C. and treated with HCl gas. A solid formed immediately, the mixture was stirred for 2 hours and then filtered. The solid was dried to yield 0.45 g of the title compound, mp >250° C.;

NMR (DMSO-d$_6$): δ 9.40 (bs, 4H), 7.66 (d, 2H), 7.51 (dd, 2H), 7.42 (m, 4H), 3.84 (m, 4H), 3.41 (m, 4H), 3.20 (m, 4H), 3.08 (m, 4H).

EXAMPLE 117

{2-[2-(pyrrolidine-1-carbonyl)-phenydisulfanyl]-phenyl}-pyrrolidin-1-yl-methanone This compound was prepared according to the general method of Example 112 using 2,2'-dithiobisbenzoyl chloride (1.0 g, 3.0 mmol) in 15 mL of dichloromethane and pyrrolidine (0.63 mL, 7.5 mmol) and triethylamine (1.2 mL, 9 mmol) in 20 mL of dichloromethane, to give 0.75 g of the title compound as a foam, mp 62–63° C.;

NMR (CDCl$_3$): δ 7.65 (d, 2H), 7.28 (m, 2H), 7.21 (m, 4H), 3.63 (t, 4H), 3.19 (t, 4H), 1.92 (q, 4H), 1.83 (q, 4H).

EXAMPLE 118

{2-[2-(3-Hydroxy-pyrrolidine-1-carbonyl)-phenyl disulfanyl]-phenyl}-(3-hydroxy-pyrrolidin-1-yl)-methanone This compound was prepared according to the general method of Example 112 using 2,2'-dithiobisbenzoyl chloride (1.0 g, 3.0 mmol) in 15 mL of dichloromethane and 3-hydroxypyrrolidine hydrochloride (0.93 g, 7.5 mmol), triethylamine (2.3 mL, 16 mmol) in 20 mL of dichloromethane. The crude product was chromatographed (SiO$_2$, CHCl$_3$/MEOH; 95/5) to give 0.21 g of the title compound as a foam, mp 168–172° C.;

NMR (CDCl$_3$): δ 7.70 (dd, 2H), 7.36–7.19 (m, 6H), 4.51 (bs, 2H), 4.36 (bs, 2H), 3.67 (m, 4H), 3.41–3.15 (m, 6H), 1.91 (m, 4H).

EXAMPLE 119

{2-[2-(3-Hydroxymethyl-pyrrolidine-1-carbonyl)-phenyl disulfanyl]-phenyl}-(3-hydroxymethyl-pyrrolidin-1-yl)-methanone This compound was prepared according to the general method of Example 112 using 2,2'-dithiobisbenzoyl chloride (1.0 g, 3.0 nmnol) in 15 mL of dichloromethane and 3-hydroxymethylpyrrolidine (0.76 g, 7.5 mmol), triethylamine (1.2 mL, 9 mmol) in 20 mL of dichloromethane, to give 0.65 g of the title compound as a foam, mp 169–171° C.;

NMR (CDCl$_3$): δ 7.78 (m, 2H), 7.36 (m, 2H), 7.30 (m, 4H), 3.60 (m, 8H), 3.20 (m, 4H), 2.42 (m, 2H), 2.03 (m, 2H), 1.72 (m, 4H).

EXAMPLE 120

1,1'-[dithiobis(2,1-phenylenecarbonyl)]bis-4-piperidine carboxylic acid

Isonipecotic acid (4-piperidinecarboxylic acid) (0.76 g, 6 mmol), N-methyl-N-trimethylsilylacetamide and 3 drops of pyridine were stirred at room temperature for 2 hours. This suspension was added to a filtered solution of 2,2'-dithiobisbenzoyl chloride (1.0 g, 3.0 mmol) in 15 mL of dichloromethane. The solvent was removed after 18 hours and the residue was triturated with 1N HCl. The acid was decanted and the residue was dissolved in acetonitrile. After standing for 24 hours a precipitate formed. The solid was collected and dried to give 0.56 g of the title compound, mp >250° C.;

NMR (DMSO): δ 12.37 (bs, 2H), 7.65 (m, 2H), 7.45 (dd, 2H), 7.34 (m, 4H), 4.33 (d, 2H), 3.26 (m, 4H), 2.98 (m, 4H), 1.92 (d, 2H), 1.70 (d, 2H), 1.50 (m, 4H).

EXAMPLE 121

[S-(R*,R*)]-1H-Pyrrolidine-2-carboxylic acid, 1,1'-[dithiobis(2,1-phenylenecarbonyl)]bis-,bis(1,1-dimethylethyl) ester This compound was made according to the general method of Example 111 using 2,2'-dithiobisbenzoyl chloride (1.0 g, 3.0 mmol) in 15 mL of dichloromethane and proline-t-butyl ester (1.08 g, 6.3 mmol), N-methylmorpholine (0.99 mL, 9.0 mmol) in 15 mL of dichloromethane. After chromatography (SiO$_2$, CHCl$_3$/MEOH; 98/2), 1.59 g of the title compound was isolated as a solid, mp 60–64° C.;

NMR (CDCl$_3$): δ7.70 (m, 2H), 7.33 (m, 4H), 7.24 (m, 2H), 4.57 (m, 1H), 4.07 (m, 1H), 3.79 (m, 2H), 3.48 (m, 2H), 3.31 (m, 2H), 2.29 (m, 1H), 1.99 (m, 3H), 1.51 (s, 9H), 1.46 (s, 9H).

EXAMPLE 122

[S-(R*,R*)]-1,1'-[Dithiobis(2,1-phenylenecarbonyl)] bis-1H-pyrrolidine-2-carboxylic acid A solution of [S-(R*,R*)]-1H-pyrrolidine-2-carboxylic acid, 1,1'-[dithiobis(2,1-phenylenecarbonyl)]bis-,bis(1,1-dimethylethyl) ester, (1.36 g, 2.2 mmol) from Example 121 in 5 mL of dichloromethane was treated with 5 mL of trifluoroacetic acid. The mixture was stirred for 18 hours concentrated to an oil and triturated with ether and water. The gummy residue was dissolved in methanol dried over MgSO$_4$ and concentrated to a solid. The solid was triturated with dichloromethane, filtered and the filtrate was evaporated to yield 0.78 g of the title compound as a foam, mp 89–90° C. (dec);

NMR (CDCl$_3$): δ 7.71 (d, 2H), 7.43–7.20 (m, 6H), 4.76 (m, 2H), 3.28 (m, 4H), 2.39 (m, 2H), 2.18 (m, 2H), 2.10–1.85 (m, 4H).

EXAMPLE 123

[S-(R*,R*)]-N,N'-[Dithiobis(2,1-phenylenecarbonyl-1,3-pyrrolidinyl)]bis-carbamic acid, bis(1,1-dimethylethyl) ester This compound was prepared according to the general method of Example 112 using 2,2'-dithiobisbenzoyl chloride (1.0 g, 3.0 mmol) in 15 mL of dichloromethane and BOC-3-amino-1H-pyrrolidine (1.4 g, 7.7 mmol), triethylamine (1.2 mL, 9.0 mmol) in 20 mL of dichloromethane. The mixture was stirred for 18 hours and chromatographed (SiO$_2$, CHCl$_3$/MEOH; 95/5) to yield 0.51 g of the title compound as a foam, mp 115–118° C.;

NMR (CDCl$_3$): δ 7.73 (m, 2H), 7.36(m, 2H), 7.25 (m, 4H), 5.15 (bs, 2H), 4.23 (m, 2H), 3.90–3.12 (m, 8H), 2.18 (m, 2H), 1.86 (m, 2H), 1.47 (s, 18H)

EXAMPLE 124

4,4'-Dithiobis(2-phenylenecarbonyliminomethylene) bisbenzoic acid

4-Aminomethylbenzoic acid (0.95 g, 6.3 mmol) in 15 mL of 1,1,1,3,3,3-hexa methyldisilazane was heated to reflux for 2 hours, a solution was obtained. This solution was cooled, concentrated, dissolved in 15 mL of dichloromethane and filtered into a solution of 2,2'-dithiobisbenzoyl chloride (1.0 g, 3.0 mmol) in 15 mL of dichloromethane. After 18 hours the mixture was concentrated, the residue was triturated with hot ethanol and filtered. The solid was dried to yield 0.60 g of the title compound, mp >250° C.;

NMR (DMSO): δ 12.85 (bs, 2H), 9.24 (t, 2H), 7.87 (d, 4H), 7.68 (d, 2H), 7.60 (d, 2H), 7.43 (m, 6H), 7.27 (t, 2H), 4.51 (d, 4H).

EXAMPLE 125

2,2'-Dithiobis(N-acetyl-N-methyl)benzamide

N-methyl-N-trimethylsilylacetamide (2.4 mL, 15 mmol) and pyridine (0.1 mL) were added to a solution of 2,2$^1$-dithiobisbenzoyl chloride (1.0 g, 3.0 mmol) in 15 mL of dichloromethane. The solution was stirred for 18 hours and concentrated to an oil. The oily residue was triturated with 1N HCL and then chromatographed (SiO$_2$, CHCl$_3$) to yield 0.41 g of the title compound as an oil;

NMR (CDCl$_3$): δ 7.68 (dd, 2H), 7.38 (m, 2H), 7.29 (m, 4H), 3.06 (s, 6H), 2.36 (s, 6H).

EXAMPLE 126

N,N'-Bis[dithiobis(2,1-phenylenecarbonyl)bis[6-[[(1,1-dimethylethoxy)carbonyl]amino]-L-norleucine]bis (1,1-dimethylethyl) ester This compound was prepared according to the general method of Example 111 using 2,2'-dithiobisbenzoyl chloride (1.0 g, 3.0 mmol) in 15 mL of dichloromethane and N-BOC-lysine-t-butyl ester hydrochloride (2.24 g, 6.6 mmol), N-methylmorpholine (1.65 g, 15 mmol) in 20 mL of dichloromethane. The compound was purified by chromatography (SiO$_2$, CHCl$_3$/MEOH; 95/5) to yield 2.25 g of the title compound as a foam, mp 81–83° C.;

NMR (CDCl$_3$): δ 7.72 (d, 2H), 7.52 (d, 2H), 7.32 (t, 2H), 7.18 (t, 2H), 6.73 (bs, 2H), 4.63 (m, 4H), 3.07 (m, 4H), 1.93 (m, 2H), 1.76 (m, 2H), 1.45 (s, 18H).

EXAMPLE 127

N,N'-[Dithiobis(2,1-phenylenecarbonyl)bis-L-arginine-bis(1,1-dimethylethyl) ester This compound was prepared according to the general method of Example 111 using 2,2'-dithiobisbenzoyl chloride (1.0 g, 3.0 mmol) in 15 mL of dichloromethane and arginine-t-butyl ester hydrochloride (1.48 g, 6.6 mmol), N-methylmorpholine (1.65 mL, 15 mmol) in 20 mL of dichloromethane. A precipitate formed which was collected and washed with ether. The solid was treated with boiling isopropanol and filtered hot to yield 1.15 g of the title compound.

NMR (DMSO): δ 8.91 (d, 2H), 7.63 (d, 4H), 7.46 (m, 4H), 7.31 (t, 2H), 6.98 (bs, 2H), 4.60 (m, 2H), 2.70 (m, 2H), 2.57 (m, 2H), 1.41 (s, 18H).

EXAMPLE 128

N,N'-[Dithiobis(2,1-phenylenecarbonyl)bis-L-arginine

This compound was prepared according to the general method of Example 122 using N,N'-[Dithiobis (2,1-phenylenecarbonyl)bis-L-arginine-bis(1,1-dimethylethyl) ester, (1.31 g, 2.0 mmol) from Example 127 in 15 mL of dichloromethane and 15 mL of trifluoroacetic acid. The residue was triturated with ethanol and 1N HCl to yield 0.74 g of the title compound, mp 208–211° C.;

NMR (DMSO): δ 12.74 (bs, 2H), 8.85 (d, 2H), 7.67 (dd, 4H), 7.48 (t, 2H), 7.43 (bs, 2H), 7.31 (t, 2H), 6.98 (bs, 2H), 4.72 (q, 2H), 2.72 (dd, 2H), 2.60 (dd, 2H).

EXAMPLE 129

4,4'-[Dithiobis(2,1-phenylenecarbonyliminomethylene) bis-transcyclohexane carboxylic acid This compound was prepared according to the general method of Example 124 using trans 4-aminomethylcyclohexanecarboxylic acid (1.0 g, 6.3 mmol) and 2,2'-dithiobisbenzoyl chloride (1.0 g, 3.0 mmol) in 15 mL of dichloromethane. Crystallization from ethanol gave 0.66 g of the title compound as a solid, mp 230–232° C.;

NMR (DMSO): δ 12.01 (s, 2H), 8.62 (t, 2H), 7.61 (d, 4H), 7.42 (t, 2H), 7.29 (t, 2H), 3.12 (m, 4H), 2.14 (t, 2H), 1.91 (d, 4H), 1.82 (d, 4H), 1.52 (m, 2H), 1.26 (q, 4H), 1.00 (q, 4H).

EXAMPLE 130

2,2'-Dithiobis[N-(2-thienylmethyl)]benzamide

A filtered solution of 2,2'-dithiobisbenzoyl chloride (1.0 g, 3.0 mmol) in 15 mL of dichloromethane was added to a solution of 2-aminomethylthiophene (0.68 mL, 6.6 mmol) and triethylamine (1.2 mL, 9.0 mmol) in 20 mL of dichloromethane. After 10 minutes a precipitate formed, the mixture was stirred for 18 hours and filtered. The solid was washed with dichloromethane and dried to yield 0.84 g of the title compound as a solid, mp 177–178° C.;

NMR (DMSO): δ 9.30 (m, 2H), 7.64 (m, 4H), 7.40 (m, 4H), 7.29 (t, 2H), 7.05 (m, 2H), 6.98 (m, 2H), 4.63 (m, 4H).

EXAMPLE 131

2,2'-dithiobis[N-[2-(4-morpholinyl)ethyl]]benzamide

This compound was prepared according to the general method of Example 111 using 2,2'-dithiobisbenzoyl chloride (1.0 g, 3.0 mmol) and 2-aminoethylmorpholine (0.87 mL, 6.6 mmol), triethylamine (1.2 mL, 9.0 mmol) in 20 mL of dichloromethane. The mixture was chromatographed ($SiO_2$) to yield 65 mg the title compound.

EXAMPLE 132

2-[2-(4-Sulfamoylphenylcarbamoyl) phenyldisulfanyl] propionic acid

A suspension of 0.46 g (1.5 mmol) of 4-(3-oxo-3H-benzo[d]isothiazol-2-yl)benzenesulfonamide in a mixture of 15 mL of methanol and 15 mL of tetrahydrofuran was treated with 0.16 g (1.5 mmol) of thiolactic acid. The reaction mixture was heated to 50° C. for 3 hours and then at room temperature for 18 hours. The resulting solution was filtered through a fiber glass pad to clarify and the filtrate was evaporated in vacuo. The residue was triturated with ether and the solid was removed by filtration. After washing with ether, the solid was dried in vacuo to give 0.58 g of the title compound, mp 268–270° C.

EXAMPLE 133

2-Acetylamino-3-[2-(4-sulfamoylphenylcarbamoyl) phenyl disulfanyl]-propionic acid, methyl ester A solution of 20 mL of methanol and 20 mL of tetrahydrofuran was cooled to 0° C. and treated dropwise with 1.31 g (10 mmol) of chlorocarbonyl-sulfenyl chloride. The reaction mixture was stirred at 0° C. for 15 minutes and 3.0 g (9.7 mmol) of solid 2-thio-N-(4-sulfamoylphenyl)benzamide was added. The mixture was stirred at 0° C. for 0.5 hours and then at room temperature for 4 hours. The resulting solution was treated with 1.63 g (10 mmol) of N-acetyl-L-cysteine and heated to 60° C. for 0.5 hours. The solvent was removed in vacuo and the residue was triturated with water. The solid was removed by filtration, washed with water, ether and dried in vacuo to give 4.3 g of the title compound, mp 138–140° C.

EXAMPLE 134

2-Acetylamino-3-[2-(4-sulfamoylphenylcarbamoyl) phenyldisulfanyl]-propionic acid This compound was prepared according to the method of Example 132 using 0.8 g (2.4 mmol) of 4-(3-oxo-3H-benzo[d]isothiazol-2-yl)benzenesulfonamide and 0.39 g (2.4 mmol) of N-acetyl-L-cysteine. The product was washed with ether and dried in vacuo to give 0.92 g of the title compound, mp 218–220° C.

EXAMPLE 135

{2-[2-(4-Sulfamoylphenylcarbamoyl) phenyldisulfanyl] propionylamino}-acetic acid This compound was prepared according to the method of Example 132 using 0.46 g (1.5 mmol) of 4-(3-oxo-3H-benzo[d]isothiazol-2-yl)benzenesulfonamide and 0.25 g (1.5 mmol) of 2-mercapto-propionylglycine. The product was washed with ether and dried in vacuo to give 0.65 g of the title compound, mp 254–256° C.

EXAMPLE 136

2-[2-(4-Sulfamoylphenylcarbamoyl) phenyldisulfanyl] benzoic acid

This compound was prepared according to the method of Example 132 using a suspension of 0.46 g (1.5 mmol) of 4-(3-oxo-3H-benzo[d]isothiazol-2-yl)benzene sulfonamide in a mixture of 15 mL of methanol and 15 mL of tetrahydrofuran, and 0.23 g (1.5 mmol) of thiosalicylic acid. The product was washed with ether and dried in vacuo to give 0.66 g of the title compound, mp 276–278° C.

EXAMPLE 137

2-[2-(4-Sulfamoylphenylcarbamoyl) phenyldisulfanyl] benzoic acid, methyl ester

This compound was prepared according to the method of Example 132 using a suspension of 0.46 g (1.5 mmol) of 4-(3-oxo-3H-benzo[d]isothiazol-2-yl)benzene sulfonamide in a mixture of 15 mL of methanol and 15 mL of tetrahydrofuran, and 0.27 g (1.6 mmol) of methyl thiosalicylate. The product was triturated with ether, filtered, washed with ether and dried in vacuo to give 0.66 g of the title compound, mp 288–290° C.

EXAMPLE 138

2-Amino-3-methyl-3-[2-(4-sulfamoylphenylcarbamoyl) phenyldisulfanyl]-butyric acid This compound was prepared according to the method of Example 132 using a suspension of 0.46 g (1.5 mmol) of 4-(3-oxo-3H-benzo[d]isothiazol-2-yl)benzene sulfonamide in a mixture of 15 mL of methanol and 15 mL of tetrahydrofuran, and 0.3 g (1.6 mmol) of D(−)-penicillinamine hydrochloride. The crude product was dissolved in 2-propanol (20 mL) and precipitated by the addition of 80 mL of ether. The precipitate was removed by filtration, dissolved in 30 mL water, filtered through a fiber glass pad and freeze dried to give 0.35 g of the title compound, mp 115–118° C.

EXAMPLE 139

2-Amino-3-methyl-3-[2-(4-sulfamoylphenylcarbamoyl) phenyldisulfanyl]-butyric acid, methyl ester This compound was prepared according to the method of Example 132 using a suspension of 0.61 g (2.0 mmol) of 4-(3-oxo-3H-benzo[d]isothiazol-2-yl)benzene sulfonamide in a mixture of 10 mL of methanol and 10 mL of tetrahydrofuran, and 0.44 g (2.2 mmol) of D(−)-penicillinamine methyl ester hydrochloride. The crude product was dissolved in 20 mL of 2-propanol and precipitated by the addition of 100 mL of ether. The precipitate was removed by filtration, dissolved in water, filtered through a fiber glass pad and freeze dried to give 0.54 g of the title compound, mp 140–142° C.

EXAMPLE 140

2-(2,3-Dihydroxypropyldisulfanyl)-N-(4-sulfamoylphenyl) benzamide

This compound was prepared according to the method of Example 132 using a suspension of 0.46 g (1.5 mmol) of 4-(3-oxo-3H-benzo[d] isothiazol-2-yl) benzenesulfonamide in a mixture of 15 mL of methanol, and 15 mL of tetrahydrofuran and 2,3-dihydroxy-1-propanethiol. The product was washed with ether and dried in vacuo to give 0.61 g of the title compound, mp >260° C.

EXAMPLE 141

2-[2-(Acetylmethylamino)-1-phenylpropyldisulfanyl]-N-(4-sulfamoyl-phenyl) benzamide This compound was prepared according to the method of Example 132 using a suspension of 0.46 g (1.5 mmol) of 4-(3-oxo-3H-benzo[d]isothiazol-2-yl)benzene sulfonamide in a mixture of 15 mL of methanol and 15 mL of tetrahydrofuran, and 0.34 g (1.5 mmol) of N-(2-mercapto-1-methyl-2-phenylethyl)-N-methylacetamide. The product was washed with ether and dried in vacuo to give 0.74 g of the title compound, mp 240–242° C.

EXAMPLE 142

2,2'-Dithiobis[N-[4-(aminosulfonyl)phenyl]methyl] benzamide

A solution of 1.86 g (10 mmol) of N-methyl sulfanilamide in 25 mL of tetrahydrofuran was treated with 1.01 g (10 mmol) of N-methyl-morpholine and cooled to 0° C. The resulting solution was treated rapidly, dropwise with a solution of 1.72 g (5.0 mmol) of 2,2'-dithiobisbenzoyl chloride in 25 mL of dichloromethane maintaining the temperature at 0° C. The reaction was stirred at 0° C. for 2 hours and then at room temperature for 18 hours. The solvent was removed in vacuo and the residue was partitioned between ethyl acetate/water. The organic layer was washed with 1.0M hydrochloric acid, water, dried (MgSO$_4$), filtered and evaporated in vacuo. The residue was heated in dichloromethane for 4 hours and the solids were removed by filtration, washed with dichloromethane and dried in vacuo to give 1.94 g of the title compound, mp 243–245° C.

EXAMPLE 143

2-[2-(2-Acetylamino-2-carboxyethyldisulfanyl) benzoylamino]-3-methyl-pentanoic acid A solution of 0.58 g (2.2 mmol) of [S-(R*,R*)]-3-methyl-2-(3-oxo-3H-benzo[d]isothiazol-2-yl)pentanoic acid in 20 mL of methanol was treated with 0.36 g (2.2 mmol) of N-acetyl-L-cysteine and the reaction was stirred at room temperature for 18 hours. The solvent was removed in vacuo and the residue was triturated with 100 mL of 60° C. water. The water was decanted and the solid was dissolved in 50 mL of ethyl acetate. The organic solution was dried (MgSO$_4$), filtered and evaporated in vacuo to give the title compound as a white, solid foam, mp 85–90° C.

EXAMPLE 144

2,2'-Dithiobis[N-(phenylsulfonyl)-benzamide

This compound was prepared according to the method of Bartlett (R. G. Bartlett, L. E. Hart and E. W. McClelland, *J. Chem. Soc.*, 1939:760).

EXAMPLE 145

2,2'-Dithiobis[N-[4-(aminosulfonyl)phenyl]-benzene sulfonamide

To a solution of 4-aminosulfonyl aniline (1.1 g, 6.4 mmol) in pyridine (15 mL) was added a solution of 2,2'-dithiobis-benzenesulfonyl chloride (1.0 g, 2.4 mmol, prepared according to Gialdi, *Farmaco Ed. Sci.*, 1959;14:751 at 0° C. under a nitrogen atmosphere. The resulting orange solution was allowed to warm to room temperature over 48 hours. This solution was then partitioned between ethyl acetate and water. The ethyl acetate solution was washed extensively with water and brine. This solution was then dried (MgSO$_4$), filtered and then concentrated in vacuo. The residue was then flash chromatographed on silica gel (70% ethyl acetate:30% hexane) to give 0.65 g of a solid which was contaminated with a small amount of 4-aminosulfonyl aniline. Recrystallization of this material gave 0.36 g of the title product as a white solid, mp 167–175° C. (dec.);

NMR (DMSO-d$_6$): δ 11.4 (s, 2H), 8.05 (m, 2H), 7.7 (m, 4H), 7.6 (m, 2H), 7.2–7.4 (m, 12H) ppm.

EXAMPLE 146

2,2'-Dithiobis[N-(4-nitrophenyl)]-benzenesulfonamide

This compound was prepared according to the general procedure of Example 145 using 4-nitro aniline, mp >220° C.;

NMR (DMSO-d$_6$) δ 11.9 (s, 2H), 8.1 (m, 4H), 8.05 (m, 2H), 7.7 (m, 2H), 7.3–7.5 (m, 8H) ppm.

EXAMPLE 147

2,2'-Dithiobis[N-(4-methoxyphenyl)]-benzenesulfonamide

This compound was prepared according to the general procedure of Example 145 using 4-methoxy aniline, mp 150–160° C. (dec.);

NMR (DMSO-d$_6$): δ 10.4 (s, 2H), 7.85 (m, 2H), 7.6 (m, 2H), 7.4 (m, 4H), 7.0 (m, 4H), 6.8 (m, 4H), 3.65 (s, 6H) ppm.

EXAMPLE 148

2,2'-Dithiobis[5-chloro]-benzenesulfonamide

To 5.1 g (22.9 mmol) of 2-mercapto-5-chlorobenzenesulfonamide in 100 mL of acetic acid was added 1.2 mL of bromine and the mixture stirred for 3 hours. The solides that formed were collected by filtration, washed with cold acetic acid, then ether. The crude product was recrystallized from acetone to give 2.4 g of the title compound, mp 184–285° C.

EXAMPLE 149

[2-(2-Benzoyl-phenyldisulfanyl)-phenyl]-phenylmethanone

To a solution of 2-mercaptobenzophenone (2.3 g, 7.4 mmol) in diethyl ether (10 mL) was added dropwise diethyl azodicarboxylate (0.65 g, 3.7 mmol). The solution was stirred for 5 minutes at room temperature, then diluted with benzene (40 mL) and refluxed for 16 hours. The solution was cooled and concentrated in vacuo leaving a yellow liquid. The crude product was purified using silica gel chromatography (75% hexane/25% ethyl acetate) to give the title compound as a yellow foam (0.8 g, 50%);

NMR (CDCl$_3$): δ 7.9 (d, 2H), 7.8 (d, 4H), 7.6 (t, 2H), 7.5–7.3 (m, 8H), 7.2 (t, 2H) ppm.

EXAMPLE 150

{2-[2-(hydroxyimino-phenyl-methyl)-phenyldisulfanyl]-phenyl}-phenyl-methanone

The [2-(2-benzoyl-phenyldisulfanyl)-phenyl]-phenyl-methanone (0.55 g, 1.2 mmol) was diluted with ethanol (5 mL) and anhydrous pyridine (5 mL). Hydroxylamine hydrochloride (1 g, 14 mmol) was added and the solution was refluxed for 90 minutes. The solution was cooled and poured into cold aqueous HCl (1N). Ethyl acetate was added, the layers were separated, and the organic portion was washed with brine, dried (MgSO$_4$), and filtered. The filtrate was concentrated to dryness and the residue was triturated with 75% hexane/25% ethyl acetate to give the title compound (0.19 g, 32%) as a white solid, mp 191–193° C.;

NMR (CDCl$_3$): δ 7.6 (d, 2H), 7.4 (d, 4H), 7.3–7.1 (m, 10H), 7.0 (d, 2H) ppm.

The compounds of this invention have been found to be active as antibacterial agents and as antiviral agents. The compounds are thus useful as pharmaceuticals as well as industrial disinfectants.

The compounds of the present invention cause the extrusion of zinc from the nucleocapsid protein (NCp7) of HIV-1. The NC protein is highly conserved among all retroviruses (South T., Blake P., et al., *Biochemistry*, 1990;29:7786) and is essential for viral infectivity (Aldovini A. and Young R., *J. Virology*, 1990;64:1920 and Gorelick R., Nigida S., et al., *J. Virology*, 1990;64:3207). The zinc is normally held in NC proteins by 1 or 2 zinc fingers. In the case of HIV-1, 2 zinc fingers are present (Summers M., South T., et al., *Biochemistry*, 1990;29:329) and are involved specifically with the PSI site on viral RNA which controls the packaging of viral RNA. Interference of this packaging causes the formation of non-infectious virions (Dannull J., Surovoy A., et al., *EMBO*, 1994;13:1525). It has previously been shown that compounds that cause zinc extrusion have potent anti-HIV activity in multiple cell lines and against all retroviruses (Rice W., Schaeffer C., et al., *Nature*, 1993;361:473).

A fluorescence-based assay has been developed to monitor the ejection of zinc from purified HIV-1 NCp7. The fluorophore, N-(6-methoxy-8-quinolyl)-p-toluenesulfonamide (TSQ), has an increased fluorescent signal upon bonding zinc ion in solution. The NCp7 protein containing 2 Zn-fingers and 2 Zn ions is incubated with drug causing the extrusion of Zn ions. The released Zn is then sequestered by the TSQ and the increased fluorescence monitored relative to control. The assay was performed as follows: 10 μM compound was added to 2.8 μM NCp7 and 47 μM TSQ in 20 μL of pH 7.4 buffer at 26° C. for 90 minutes. Fluorescence (excitation 355 nM emission 400 nM) was monitored versus time. Controls were the NCp7 under assay conditions without drug, and apo NCp7 (no Zn) with drug. The % Zn extrusion was calculated based on the actual fluorescence measured divided by the fluorescence of all theoretical Zn extruded (5.6 μM)×100.

Electrospray ionization mass spectral analysis was also performed. Using 40 μM NCp7 in ammonium acetate buffer at pH 6, and 320 μM 2-[[2-[(1-carboxy-2-methylbutylcarbamoyl)-phenyldisulfanyl]-benzoyl]-amino]-3-methylpentanoic acid (Example 5) in acetonitrile was added. After 2 minutes, a mass peak at 6366 (18%) corresponding to apo NCp7 (loss of 2 Zn) appeared. In addition, a peak at 6698 (100%) corresponding to the NCp7+266+Zn appeared. This peak represents the NCp7 with one zinc extruded and a covalently attached compound of 266 MW corresponding exactly to one-half the MW of Example 5 indicating the extrusion of zinc and the formation of a covalent bond between the cysteine of the zinc finger and one-half of the disulfide of Example 5. The new disulfide corresponds to the formula Protein S—S—[structure: 2-substituted benzamide with CO$_2$H and sec-butyl group on NH]

Mol. wt. 6698

The test systems utilized to establish the antiviral activity of the arylthio compounds of this invention are well recognized in the art and are routinely employed for such purpose. For example, the assay utilized to evaluate the compounds activity against the HIV virus is that employed by the U.S. National Cancer Institute as described by Weislow O. S., et al., *J. Natl. Cancer Inst.*, 1989;81:577–586, incorporated herein by reference.

The procedure is designed to detect agents acting at any stage of the virus reproductive cycle. The assay basically involves the killing of T4 lymphocytes by HIV. Small amounts of HIV are added to cells, and at least two complete cycles of virus reproduction are necessary to obtain the required cell killing. Agents which interact with virions, cells, or virus geneproducts to interfere with viral activities will protect cells from cytolysis. The system is automated in several features to accommodate large numbers of candidate agents, and is generally designed to detect anti-HIV activity. However, compounds which degenerate or are rapidly metabolized in the culture conditions may not show activity in this screen.

Another test system utilized to evaluate the invention compounds is called HIV H9 assay. The HIV H9 cell assay measures the inhibitor concentration required to suppress HIV-1 virus replication. In this system, viral growth occurs through multiple rounds of the life-cycle. Any suppression of the replication kinetics results in a geometric decrease in virus production. As a result, this assay is a sensitive means of measuring the ability of a compound to inhibit HIV-1 viral replication.

The H9 T-cell line is batch infected with HIV virus at an MOI of 0.01. After 2 hours absorption, the cells are washed, resuspended in RPMI-1640/10% fetal calf serum, and seeded at 5×10-3 cells/well of a 96-well plate. A duplicate plate of uninfected H9 cells is prepared for the cytotoxicity assay. Drugs are serially diluted ⅓.16 in DMSO, transferred to media at an 8× concentration, and then added to the cultures in triplicate. The final DMSO concentration of 0.002 (0.20%).

Viral production is measured by RT assay and cytotoxicity is measured by XTT assay at 7 days post-infection. The RT assay is performed as a modification of Borroto-Esoda and Boone, *J. Virol.*, 1991;65:1952–1959 and quantitated using a Molecular Dynamics Phosphoimager with Imagequant software. The XTT assay is performed as a modification of Roehm, et al., *J. Immuno. Methods.*, 1991;142:257–265 and quantitated using a molecular Devices Thermomax plate reader with Softmax software.

Data is electronically transferred to a Microsoft Excell spreadsheet for analysis. The RT assay values equivalent to 50% and 90% inhibition of virus production are calculated from the untreated controls. The concentrations of inhibitor required to produce these values (IC$_{50}$ and IC$_{90}$) are interpolated from data points flanking these RT activities. The XTT assay values equivalent to 50% cytotoxicity are calculated from the untreated controls. The concentrations of inhibitor required to produce this value are interpolated from data points flanking these XTT values.

Yet another test system employed to determine antiviral activity is called the CEM cell assay.

T4 lymphocytes (CEM cell line) are exposed to HIV at a virus to cell ratio approximately 0.05, and plated along with noninfected control cells in 96-well microliter plates.

The candidate agent is dissolved in dimethyl sulfoxide (unless otherwise noted), then diluted 1:200 in cell culture medium. Further dilutions (half-$\log_{10}$) are prepared before adding to an equal volume of medium containing either infected or noninfected cells.

Cultures are incubated at 37° in a 5% carbon dioxide atmosphere for 6 or 7 days. The tetrazolium salt, XTT, is added to all wells, and cultures are incubated to allow formazan color development by viable cells (*J. National Cancer Institute*, 1989;81:577–586). Individual wells are analyzed spectrophotometrically to quantitate formazan production, and in addition are viewed microscopically for detection of viable cells confirmation of protective activity.

Drug-tested virus-infected cells are compared with drug-treated noninfected cells and with other appropriate controls (untreated infected and untreated noninfected cells, drug-contain wells without cells, etc.) on the same plate. Data are reviewed in comparison with other tests done at the same time and a determination about activity is made.

Table 1 below presents data for several invention compounds evaluated in the zinc extrusion assay described above.

TABLE 1

Zinc Extrusion From the Zinc Fingers of
HIV-1 Nucleocapsid Protein (NCp7)

| Compound of Example | % Zinc Extrusion Relative to Control |
|---|---|
| EDTA[a] | 10 |
| Reference Compound[b] | 0 |
| 1 | 20 |
| 3 | 73 |
| 4 | 87 |
| 5 | 87 |
| 9 | 77 |
| 12 | 27 |
| 15 | 72 |
| 18 | 67 |
| 25 | 73 |
| 56 | 73 |
| 60 | 65 |
| 62 | 73 |
| 68 | 89 |
| 70 | 74 |
| 74 | 59 |
| 75 | 52 |
| 76 | 82 |
| 84 | 50 |
| 94 | 62 |
| 113 | 67 |
| 132 | 70 |
| 133 | 53 |
| 134 | 77 |
| 135 | 40 |
| 139 | 70 |
| 142 | 84 |
| 145 | 65 |

TABLE 1-continued

Zinc Extrusion From the Zinc Fingers of
HIV-1 Nucleocapsid Protein (NCp7)

| Compound of Example | % Zinc Extrusion Relative to Control |
|---|---|
| 148 | 92 |
| 150 | 36 |

[a]EDTA extrudes 10% of the zinc in 24 hours. All the extrusion data for the invention compounds was obtained in 90 minutes.
[b]This compound is 4,4'-dithiobis-4'-sulfamoyl benzanilide. It was prepared as in Example 1 using 4,4'-dithiobisbenzoyl chloride and the 4-sulfalfamoylaniline.

Table 2 below presents data for several invention compounds when evaluated in the H9 and the CEM cell assays. The data establish the compounds of this invention are effective against the HIV virus when evaluated in both test systems.

TABLE 2

Anti-HIV-1 Activity

| | H9 Cell Assay | | CEM Cell Assay | |
|---|---|---|---|---|
| Compound of Example No. | $EC_{50}{}^a$ ($\mu$M) | $IC_{50}{}^b$ ($\mu$M) | $EC_{50}{}^a$ ($\mu$M) | $IC_{50}{}^b$ ($\mu$M) |
| Reference Compound[c] | >100 | >100 | >100 | >100 |
| 1 | 0.7 | 36 | 2.9 | >120 |
| 4 | 4.8 | 27 | | |
| 5 | 1.4 | 62 | 10.5 | 105 |
| 6 | 2.5 | 28 | 5.2 | >100 |
| 9 | 1.70 | >100 | 5.2 | >120 |
| 10 | 5.40 | >100 | | |
| 12 | | | 0.59 | 21 |
| 15 | 2 | 22 | | |
| 16 | | | 2.5 | 66 |
| 19 | | | 2.4 | >100 |
| 23 | | | 4.3 | >100 |
| 48 | | | 18 | >100 |
| 51 | | | 8.4 | 64 |
| 54 | | | 6.9 | 75 |
| 57 | | | 6.0 | 71 |
| 68 | | | 25 | >100 |
| 73 | | | 5.0 | 70 |
| 74 | | | 6.3 | 67 |
| 75 | | | 5.3 | 59 |
| 76 | | | 6.2 | >100 |
| 102 | | | 1.7 | 68 |
| 106 | | | 1.8 | 22 |
| 108 | | | 5.9 | 61 |
| 132 | | | 2.8 | >100 |
| 133 | | | 6.7 | 69 |
| 134 | | | 6.9 | >100 |
| 135 | | | 5.8 | >100 |
| 137 | | | 8.6 | 65 |
| 138 | | | 6.3 | 66 |
| 139 | | | 6.9 | >100 |
| 142 | | | 17 | >100 |
| 148 | | | 12 | 30 |

[a]Effective Concentration which protects cells from viral cytopathic effects.
[b]Inhibitory Concentration where drug alone inhibits cell growth.
[c]4,4'-dithiobis-4'-(sulfamoylbenzanilide)

The compounds of the invention were also evaluated against various other HIV strains and cell lines utilizing the assay methodology described above. The compounds were additionally evaluated against clinical isolates of HIV strains. Table 3 presents the results of such testing, and also presents activity for the known anti-HIV agents ddI (dideoxyinosine) and AZT. The data establish the compounds of this invention are potent antiviral agents, and have excellent activity against numerous HIV strains, including some which are resistant to known treatments such as AZT.

TABLE 3

Activity vs. Other HIV Strains and Cell Lines

| Cell Line | Virus | Example 1 | Example 4 | Example 9 | ddI | AZT (nM) |
|---|---|---|---|---|---|---|
| | | $EC_{50}$ ($\mu$M) | | | | |
| CEM | HIV-1$_{RF}$ | 2.3 | 1.5 | 0.4 | — | 0.6 |
| CEM | HIV-1$_{IIIb}$ | 2.8 (4.6) | 5.2 | 0.4 | — | 4.5 |
| MT-2 | HIV-1$_{IIIb}$ | 2.6 | — | 9.4 | 6.0 | — |
| MT-2 | HIV-1$_{A17}$ | 0.6 | — | — | 4.6 | — |
| MT-4 | HIV-1$_{6R}$ | 1.9 | 1.9 | — | — | >1000 |
| MT-4 | HIV-1$_{A17}$ | 0.6 | 8.9 | 2.4 | — | 114 |
| CEM | HIV-1$_{N119}$ | 2.2 | 4.6 | 2.3 | — | 44.4 |
| CEM | HIV-2$_{ROD}$ | 2.6 | 3.0 | 1.0 | — | 1.41 |
| CEM | SIV | 14.6 | 3.4 | 2.1 | — | 245 |
| AA5 | HIV-1$_{IIIb}$ | 0.9 | — | 3.5 | — | — |
| Clinical Isolates | | | | | | |
| PBL | HIV-1$_{VIHU}$ | 3.6 | — | 5.2 | — | — |
| PBL | HIV-1$_{WEIO}$ | 3.5 | 5.2 | 7.5 | — | 3.0 |
| PBL | HIV-1$_{BAKI}$ | 0.3 (0.25) | — | 1.8 | — | — |
| PBL | HIV-1$_{WOME}$ | 4.0 | — | 5.7 | — | — |

The compounds of the invention have utility against a wide range of retroviral infections, and accordingly, have broad application. Examples of possible viruses that may be suitable for treatment using the present invention include Type C and Type D retroviruses, HTLV-1, HTLV-2, FLV, SIV, MLV, BLV, BIV, equine infectious viruses, anemia viruses, avian sarcoma viruses, and the like.

The compounds are additionally useful as broad spectrum antibiotics. Table 4 below presents typical antibacterial activity for the compounds of this invention. Minimum inhibitory concentrations were determined utilizing microtitration techniques described by Heifetz, et. al., *Antimicrobial Agents and Chemotherapy*, 1974, Vol. 6, 124. The data establish that the compounds have activity against a broad spectrum of bacteria, both Gram + and Gram −. Accordingly, the compounds can be utilized to treat and prevent bacterial diseases in animals and humans. They can also be used as industrial disinfectants, for example, to reduce bacterial growth in shower stalls and public areas.

TABLE 4

Antibacterial Activity

| Compound of Example No. | Gram (−) | | | Gram (+) | |
|---|---|---|---|---|---|
| | E. coli MC4100 | E. coli B90 | B. subtilis RBI | Stah. aureus RBI | Strep. pyogenes c-203 |
| 4 | 128 | 32 | 128 | 256 | 64 |
| 6 | 64 | 32 | 128 | 128 | 64 |

In a further embodiment of this invention, the compounds can be formulated into compositions suitable for applying to surfaces such as wood, metal, ceramic, and the like, and for administering to animals, including humans, for treating and preventing diseases caused by bacteria and viruses. The compounds can be formulated for administration by any route, for instance orally, parenterally, topically, and rectally. For oral administration, for example, an invention compound can be mixed with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5% to about 80% of the weight of the unit. The amount of active compound in such therapeutically useful compositions is such that a therapeutically effective dosage will be obtained. Preferred compositions or preparations according to the present invention are prepared so that an oral dosage unit form contains between about 5 and 1000 mg of active compound, and ideally about 25 to about 750 mg.

The tablets, troches, pills, capsules, and the like may also contain common pharmaceutical excipients such as binders, sweeteners, and the like. Typical binders include gum tragacanth, acacia, corn starch, and gelatin, as well as excipients such as dicalcium phosphate. Typical disintegrating agents include corn starch, potato starch, alginic acid, and the like. A commonly used lubricant is magnesium stearate. Typical sweetening agents are sucrose, lactose, or saccharin, and flavoring agents such as peppermint, oil of wintergreen, or cherry flavoring can be utilized. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially nontoxic in the amounts employed.

The arylthio compounds of the invention can also be formulated for topical administration, for instance as patches, salves, creams, ointments, and the like. Agents commonly utilized to enhance transdermal passage can also be employed. The compounds can also be formulated with waxes and the like for convenient rectal administration.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants. the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. Especially preferred are compositions comprising an invention compound together with one or more additional antiviral agents, for instance AZT (azidothymidine), ddI (dideoxyinosine), ribavirin, vidarabine, acyclovir, gaveiclovir, and the like.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 25 to about 750 mg being preferred. Expressed in proportions, the active compound is generally present in from about 10 to about 750 mg/mL of carrier. In the case of compositions containing supplementary active ingredients, the dosages are determined by reference to the usual dose and manner of administration of the said ingredients. The unit dosages typically will be administered from one to four times per day, or as otherwise needed to effect treatment of the disease state.

The following examples further illustrate the formulations of this invention.

EXAMPLE 151

Soft gelatin capsules were prepared using the following ingredients:

|  | Quantity (mg/capsule) |
| --- | --- |
| Compound of Example 1 | 250.0 |
| Butylated hydroxyanisole B.P. | 0.05 |
| Fractionated Coconut Oil B.P. | 70.0 |
|  | 320.05 |

The above ingredients were mixed and filled into a soft gelatin capsule, the shell components of which were gelatin and glycerine. The capsules are administered at the rate of one to four times a day.

EXAMPLE 152

Tablets are prepared using the following components:

| Compound of Example 5 | 500 | mg |
| --- | --- | --- |
| Microcrystalline Cellulose | 200 | mg |
| Sodium Carboxymethyl Starch | 20 | mg |
| Magnesium Stearate | 4 | mg |
| Butylated Hydroxyanisole B.P. | 0.002 | mg |

The ingredients were blended to uniformity and compressed into a tablet for oral administration. One to four tablets are administered daily for treatment of bacterial and viral infections.

EXAMPLE 153

An aerosol is prepared as follows:

| Compound of Example 4 | 100 | mg |
| --- | --- | --- |
| Propylene glycol | 20 | mg |
| Dichlorotetrafluoroethane (Propellant 14) | 600 | mg |
| Dichlorodifluoromethane (Propellant 12) | 500 | mg |

The components are mixed at −20° C. and placed into a sealed can equipped with a metering device.

EXAMPLE 154

A solution is prepared as follows:

| Compound of Example 6 | 5 | mg |
| --- | --- | --- |
| Water | 1 | L |
| 1N HCl | 20 | mL |

The ingredients are mixed to form a solution which can be utilized to wash shower stalls in order to prevent and eliminate bacterial growth.

A further embodiment of this invention is a method of treating, preventing, and combatting bacterial and viral infections. The method comprises administering an antibacterially effective or antivirally effective amount of a compound of this invention to a subject or surface in need of treatment. For example, the compounds of Formula I can be applied to shower stalls and public places in order to prevent, control, and combat bacterial and viral growth. The compounds can be administered to animals, especially humans, to treat and prevent bacterial and viral infections. As noted above, an effective amount of the active compound generally is about 5 to about 1000 mg per dosage unit, and ideally about 25 to about 750 mg.

The active ingredients of the therapeutic compositions and the compounds of the present invention exhibit excellent antiretrovirus activity when administered in amounts ranging from about 1.0 to about 100 mg/kg of body weight per day. A preferred dosage regimen for optimum results would be from about 2.0 to about 50 mg/kg of body weight per day, and such dosage units are employed so that a total of from about 0.2 to about 3.0 g of the active compound for a subject of about 70 kg of body weight are administered in a 24-hour period. This dosage regimen may be adjusted to provide the optimum therapeutic response and is preferably administered one to four times a day in dosages of about 250 to about 750 mg per administration. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular or subcutaneous routes.

The active compounds can be formulated as aqueous solutions and suspensions for washing surfaces such as wood, steel, ceramic, and the like in order to eliminate and control growth due to bacteria and viruses.

The compounds can be utilized in combination with other active agents. For example, a preferred method for treating retroviral infections comprises administering an invention compound along with one or more other antiviral agents. The active agents can be compounded together in a single dosage unit or can be administered separately. Other antiviral agents typically utilized include acyclovir, AZT (azidothymidine, zidovudine), ribavirin, vidarabine, ganciclovir, dideoxyinosine (ddI), and the like.

We claim:

1. A method for extruding zinc from the nucleocapsid protein $NC_p7$ of HIV-1 comprising administering to a subject in need of treatment a zinc extruding amount of a compound of Formula I

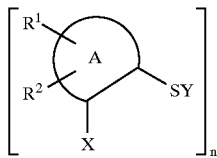

wherein:

n is 1 or 2;

X is —(C=O)—$NR^4Z$, —(C=O)—Z, or $SO_2NR^4Z$;

Y is hydrogen or SZ when n is 1, and is a single bond when n is 2;

Z is hydrogen, halo, $C_1$–$C_6$ alkyl, $COC_1$–$C_6$ alkyl, $C_3$–$C_6$ cycloalkyl-$(CR^5R^6)_m$—, phenyl$(CR^5R^6)_m$—, or Het-$(CR^5R^6)_m$—;

A is a monocyclic ring having 5 or 6 ring atoms, or a bicyclic ring having from 9 to 12 ring atoms, the ring atoms being relected from carbon and optionally up to 3 heteroatoms selected from O, S, and N;

$R^1$ and $R^2$ independently are hydrogen, halo, $C_1$–$C_6$ alkyl, $C_1$–$C_6$ alkoxy, $C_3$–$C_6$ cycloalkyl, hydroxy, nitro, cyano, phenyl-$(CR^5R^6)_m$—, Het-$(CR^5R^6)_m$—, $NR^3R^4$, $NR^3COR^4$, $CO_2R^3$, $CONR^3R^4$, $S(O)_mR^3$, $S(O)_mNR^3R^4$, or $COR^3$, or taken together are oxo (O=) or methylene dioxy (—O—$CH_2$—O—);

m is 0, 1, or 2;

$R^3$ and $R^4$ independently are hydrogen, $C_1$–$C_6$ alkyl, $C_3$–$C_6$ cycloalkyl, phenyl-$(CR^5R^6)_m$—, or Het-$(CR^5R^6)_m$—;

$R^5$ and $R^6$ independently are hydrogen, $C_1$–$C_6$ alkyl, hydroxy, COOH, amino, $CONR^7R^8$, or cyano; and $R^7$ and $R^8$ independently are hydrogen, $C_1$–$C_6$ alkyl, $C_3$–$C_6$ cycloalkyl, or phenyl;

wherein the foregoing alkyl, cycloalkyl, phenyl, and Het groups may optionally be substituted with from 1 to 3 group selected from halo, $C_1$–$C_6$ alkyl, $C_1$–$C_6$ alkoxy, trifluoromethyl, hydroxy, cyano, nitro, $NR^3R^4$, $NR^3COR^4$, $CO_2R^3$, NH(C=NH)$NH_2$, $CONR^3R^4$, $S(O)_mR^3$, $PO(OR^3)_3$, $S(O)_mNR^3R^4$, and $COR^3$, where m, $R^3$, and $R^4$ are as defined above;

or a pharmaceutically acceptable salt or solvate thereof.

2. A method according to claim 1 employing a compound of Formula I wherein A is

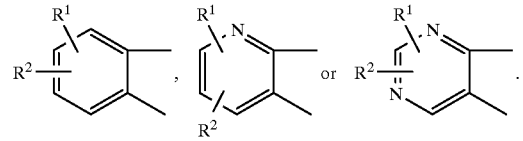

3. A method according to claim 2 employing a compound of Formula Ia

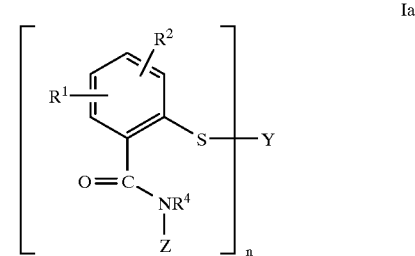

wherein:

n is 1 or 2;

Y is hydrogen when n is 1, and is a single bond when n is 2;

$R^1$ and $R^2$ independently are hydrogen, halo, $C_1$–$C_6$ alkyl, hydroxy, $C_1$–$C_6$ alkoxy, carboxy, $C_1$–$C_6$ alkoxycarbonyl, nitro, or $NR^3R^4$, where $R^3$ and $R^4$ independently are hydrogen or $C_1$–$C_6$ alkyl;

Z is hydrogen, $C_1$–$C_6$ alkyl, $C_3$–$C_6$ cycloalkyl, where said alkyl and cycloalkyl groups may have 1 or 2 substituents selected from hydroxy, halo, nitro, $NR^3R^4$, and carboxy; and Z is

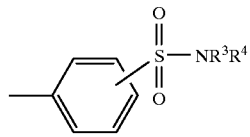

where $R^3$ and $R^4$ are as defined above;

and pharmaceutically acceptable salts and solvates thereof.

4. A method according to claim 3 employing a compound of Formula Ia wherein Z is $C_1$–$C_6$ alkyl or $C_1$–$C_6$ alkyl substituted with at least one $CO_2R^3$ group.

5. A method according to claim 4 employing a compound selected from

2-[[2-2-(1-carboxy-2-methylbutylcarbamoyl)-phenyldisulfanyl]-benzoyl]amino]-3-methylpentanoic acid,

[S-(R*,R*)]-2-[2-[2-(1-tert-Butoxycarbonyl-2-methyl-butylcarbamoyl)-6-fluoro-phenyldisulfanyl]-3-fluoro-benzoylamino]-3-methyl-pentanoic acid tert-butyl ester,

[S-(R*,R*)]-2-[2-[2-(1-tert-Butoxycarbonyl-3-methyl-butylcarbamoyl)-5-fluoro-phenyldisulfanyl]-4-fluoro-benzoylamino]-4-methyl-pentanoic acid tert-butyl ester,

[S-(R R*)-2-[2-[2-(1-tert-Butoxycarbonyl-3-methyl-butylcarbamoyl)-4-fluoro-phenyldisulfanyl]-5-fluorobenzoylamino]-4-methyl-pentanoic acid tert-butyl ester,

[S-(R*,R*)]-2-[2-[2-(1-tert-Butoxycarbonyl-3-methyl-butylcarbamoyl)-6-methoxy-phenyl-disulfanyl]-3-methoxybenzoylamino]-4-methylpentanoic acid tert-butyl ester,

[S-(R*,R*)]-2-[2-[2-(1-tert-Butoxycarbonyl-3-methyl-butylcarbamoyl)-5-methoxy-phenyldisulfanyl]-4-methoxybenzoylamino]-4-methylpentanoic acid tert-butyl ester,

[S-(R*,R*)]-2-[2-(2-(1-tert-Butoxycarbonyl-3-methylbutylcarbamoyl)-4-methoxy-phenyldisulfanyl]-5-methoxybenzoylamino]-4-methylpentanoic acid tert-butyl ester,

[S-(R*,R*)]-2 -[2-[2-(1-tert-Butoxycarbonyl-3-methylbutylcarbamoyl)-6-methyl-phenyldisulfanyl]-3-methylbenzoyl-amino]-4-methyl-pentanoic acid tert-butyl ester,

[S-(R*,R*)]-2-[2-[2-(1-tert-Butoxycarbonyl-3-methyl-butylcarbamoyl)-5-methyl-phenyl disulfanyl]-4-methylbenzoylamino]-4-methyl-pentanoic acid tert-butyl ester,

[S-(R*,R*)]-2-[2-[2-(1-tert-Butoxycarbonyl-3-methyl-butylcarbamoyl)-3-methyl-phenyl disulfanyl]-6-methylbenzoylamino]-4-methyl-pentanoic acid tert-butyl ester,

[S-(R*,R*)]-{2-[2-(1,2-Bis-tert-butoxycarbonyl-ethylcarbamoyl)-phenyldisulfanyl]-benzoylamino}-succinic acid di-tert-butyl ester,

[S-(R*,R*)]-2-{2-[2-(1,3-Bis-tert-butoxycarbonyl-propylcarbamoyl)-phenyldisulfanyl]-benzoylamino}-pentanedioic acid di-tert-butyl ester,

[S-(R*,R*)-2-{2-[2-(1,4-Bis-tert-butoxycarbonyl-butylcarbamoyl)-phenyldisulfanyl]-benzoylamino}-hexanedioic acid di-tert-butyl ester,

[R-(R*,R*)](2-{2-[(tert-Butoxycarbonylphenyl-methyl)-carbamoyl]-phenyldisulfanyl}-benzoylamino)-phenyl-acetic acid tert-butyl ester, N,N'-[Dithiobis(2,1-phenylenecarbonyl)]bis L-serine bis [O-(1,1-dimethylethyl) bis (1,1'-dimethylethyl)ester, L,L-2-[(2-{2-[(1-tert-Butoxycarbonyl-3-methyl-butyl)-methyl-carbamoyl]-phenyl disulfanyl}-benzoyl)-methyl-amino]-4-methyl-pentanoic acid tert-butyl ester, 4,4'-[Dithiobis(2,1-phenylenecarbonylimino)]-bis butanoic acid bis (1,1-dimethylethyl) ester,

[S-(R*,R*)] 2-{5-Acetylamino-2-[4-acetylamino-2-(1-tert-butoxycarbonyl-3-methyl-butylcarbamoyl)-phenyl-disulfanyl]-benzoylamino}-4-methyl-pentanoic acid tert-butyl ester,

[S-(R*,R*)] 2-{5-Ethylamino-2-[4-ethylamino-2-(1-tert-butoxycarbonyl-2-methyl-butylcarbamoyl)-phenyl-disulfanyl]-benzoylamino}-3-methylpentanoic acid tert-butyl ester, L,L-2-{2-[2-(1-Carboxy-2,2-dimethyl-propylcarbamoyl)-phenyldisulfanyl]-benzoylamino}-3,3-dimethyl-butyric acid, 2-[2-(2- {2-[1-(1-Carboxy-ethylcarbamoyl)-3-methyl-butylcarbamoyl]-phenyldisulfanyl}-benzoylamino)-4-methylpentanoylamino]-propionic acid,

[S-(R*,R*)]-2-{2-[2-(1-Carboxy-2-methyl-butylcarbamoyl)-6 -fluoro-phenyldisulfanyl]-3-fluoro-benzoylamino}-3-methyl-pentanoic acid,

[S-(R*,R*)]2-{2-[2-(1-Carboxy-3-methyl-butylcarbamoyl)-5-fluoro-phenyldisulfanyl]-4-fluoro-benzoylamino}-4-methyl-pentanoic acid,

[S-(R*,R*)] 2-{2-[2-(1-Carboxy-3-methylbutylcarbamoyl)-4-fluoro-phenyldisulfanyl]-5-fluoro-benzoylamino}-4-methyl-pentanoic acid,

[S-(R*,R*)]-2-{2-[2-(1-carboxy-3-methylbutyl-carbarnoyl)-6-methoxy-phenyldisulfanyl]-3-methoxy-benzoylamino}-4-methyl-pentanoic acid,

[S-(R*,R*)] 2-{2-[2-(1-Carboxy-3-methyl-butyl carbamoyl)-5-methoxy-phenyldisulfanyl]-4-methoxybenzoylamino}-4-methyl-pentanoic acid,

[S-(R*,R*)] 2-{2-(2-(1-Carboxy-3-methyl-butylcarbamoyl)-4-methoxy-phenyldisulfanyl]-5-methoxy-benzoylamino}-4-methyl-pentanoic acid,

[S-(R*,R*)]2-{2-(2-Carboxy-3-methylbutylcarbamoyl)-6-methyl-phenyldisultanyl]-3-methyl-benzoylamino}-4-methyl-pentanoic acid,

[S-(R*,R*)] 2-{2-[2-(1-Carboxy-3-methyl-butylcarbamoyl)-5-methyl-phenyldisulfanyl]-4-methyl-benzoylamino}-4-methyl-pentanoic acid, L,L-2-{2-[2-(1-Carboxy-3-methyl-butylcarbamoyl)-3-methyl-phenyldisulfanyl]-6-methyl-benzoylamino}-4-methyl-pentanoic acid, L,L-2-[(2-{2-[(1-Carboxy-3-methyl-butyl)-methyl-carbamoyl]-phenyldisulfanyl}-benzoyl)-methyl-amino]-4-methyl-pentanoic acid,

[S-(R*,R*)] 2-{5-Acetylamino-2-[4-acetylamino-2-(1-carboxy-3-methyl-butylcarbamoyl)-phenyldisulfanyl]-benzoylamino}-4-methyl-pentanoic acid, N,N'-[Dithiobis[[5-(ethylamino)-2,1-phenylene]carbonyl]] bis-L-iso-leucine, L,L-2-{2-[2-(1,2-Dicarboxy-ethylcarbamoyl)-phenyldisulfanyl]-benzoylamino}-succinic acid, L,L-2-{2-[2-(1,3-Dicarboxy-propylcarbamoyl)-phenyl-disulfanyl]-benzoylamino}-pentanedioic acid,

[S-(R*,R*)] 2-{2-[2-(1,4-Dicarboxybutylcarbamoyl)-phenyldisulfanyl]-benzoylamino}-hexanedioic acid, 4,4'-[Dithiobis(2,1-phenylene carbonylimino)]bis-butanoic acid,

[R-(R*,R*)] (2-{2-[(Carboxy-phenyl-methyl)-carbamoyl]-phenyldisulfanyl}-benzoylamino)-phenylacetic acid,

[S-(R*,R*)] 3-tert-Butoxy-2-{2-[2-(2-tert-butoxy-1-carboxy-ethylcarbamoyl)-phenyl disulfanyl]-benzoylamino}-propionic acid, 3,3'-[Dithiobis(2,1-phenylene carbonylimino)] bis-propionic acid, and N,N'-bis[dithiobis(2,1-phenylenecarbonyl) bis[6-[[(1,1-dimethylethoxy)carbonyl]amino]-L-norleucine]bis(1,1-dimethylethyl) ester.

6. A method for extruding zinc from the nucleocapsid protein $NC_p7$ of HIV-1 comprising administering to a subject in need of treatment a zinc extruding amount of [S-(R*,R*)]-2-[2-(1-carboxy-2-methylbutylcarbomoyl)phenyl-disulfanyl]benzoylamino]-3-methyl-pentanoic acid.

* * * * *